US010610618B2

(12) United States Patent
Onodera et al.

(10) Patent No.: US 10,610,618 B2
(45) Date of Patent: Apr. 7, 2020

(54) REVASCULARIZATION GRAFT MATERIAL

(71) Applicants: Eisai R&D Management Co., Ltd., Tokyo (JP); Hiroshi Onodera, Tokyo (JP)

(72) Inventors: Hiroshi Onodera, Tokyo (JP); Eri Nishioka, Kobe (JP)

(73) Assignee: Eisai R&D Management Co., Ltd., Tokyo (JP)

(*) Notice: Subject to any disclaimer, the term of this patent is extended or adjusted under 35 U.S.C. 154(b) by 0 days.

(21) Appl. No.: 15/102,450

(22) PCT Filed: Dec. 12, 2014

(86) PCT No.: PCT/JP2014/006193
§ 371 (c)(1),
(2) Date: Jun. 7, 2016

(87) PCT Pub. No.: WO2015/093018
PCT Pub. Date: Jun. 25, 2015

(65) Prior Publication Data
US 2017/0000928 A1 Jan. 5, 2017

(30) Foreign Application Priority Data

Dec. 16, 2013 (JP) ................................ 2013-258995

(51) Int. Cl.
A61F 2/06 (2013.01)
A61L 27/58 (2006.01)
(Continued)

(52) U.S. Cl.
CPC .......... A61L 27/507 (2013.01); A61F 2/0063 (2013.01); A61F 2/062 (2013.01);
(Continued)

(58) Field of Classification Search
CPC ...... A61F 2002/072; A61F 2/06; A61F 2/062; A61F 2/07; A61F 2/0062; A61F 2/0063;
(Continued)

(56) References Cited

U.S. PATENT DOCUMENTS 3,878,565 A * 4/1975 Sauvage .................. A61F 2/06
623/1.5
4,652,264 A * 3/1987 Dumican .................. A61F 2/06
623/1.38
(Continued)

FOREIGN PATENT DOCUMENTS

CN 1535661 10/2004
CN 101069757 11/2007
(Continued)

OTHER PUBLICATIONS

International Search Report for PCT/JP2014/006193 dated Mar. 10, 2015 with English translation.
(Continued)

Primary Examiner — Seema Mathew
(74) Attorney, Agent, or Firm — Fish & Richardson P.C.

(57) ABSTRACT

Provided is a graft material capable of securing a sufficient space for regenerated tissue in the implantation site, and thereby promoting the regeneration of a blood vessel. Specifically, the present invention provides a revascularization graft material including an outer tube and an inner tube each being formed by knitting twisted yarns of biodegradable single yarns into a hollow tubular structure, wherein there is provided, in the lumen of the outer tube, at least one inner tube having an outer diameter smaller than the lumen diameter of the outer tube. The inner tube functions as a core material for the outer tube, and accordingly the revascularization graft material is excellent in kinking resistance, and the occlusion of the lumen hardly occurs.

24 Claims, 11 Drawing Sheets

(51) Int. Cl.
*A61L 27/54* (2006.01)
*A61L 27/50* (2006.01)
*A61F 2/00* (2006.01)
*A61L 27/36* (2006.01)

(52) U.S. Cl.
CPC ........... *A61L 27/3625* (2013.01); *A61L 27/54* (2013.01); *A61L 27/58* (2013.01); *A61F 2002/0068* (2013.01); *A61L 2300/414* (2013.01)

(58) Field of Classification Search
CPC .......... A61F 2/007; A61L 27/54; A61L 27/58; A61L 27/507
See application file for complete search history.

(56) References Cited

U.S. PATENT DOCUMENTS

| | | | | |
|---|---|---|---|---|
| 4,670,286 | A * | 6/1987 | Nyilas | A61F 2/06 427/2.24 |
| 4,842,575 | A * | 6/1989 | Hoffman, Jr. | A61F 2/06 106/146.1 |
| 4,857,069 | A * | 8/1989 | Kira | A61F 2/06 606/108 |
| 5,217,495 | A * | 6/1993 | Kaplan | A61F 2/06 57/225 |
| 5,376,118 | A * | 12/1994 | Kaplan | A61F 2/06 606/228 |
| 5,662,713 | A * | 9/1997 | Andersen | A61F 2/90 128/898 |
| 5,732,572 | A * | 3/1998 | Litton | A61F 2/06 623/1.5 |
| 5,800,510 | A | 9/1998 | Schmitt | |
| 5,897,587 | A | 4/1999 | Martakos et al. | |
| 5,906,641 | A * | 5/1999 | Thompson | A61F 2/07 606/191 |
| 6,547,820 | B1 * | 4/2003 | Staudenmeier | A61F 2/06 264/103 |
| 6,596,023 | B1 * | 7/2003 | Nunez | A61F 2/06 623/1.3 |
| 6,626,939 | B1 * | 9/2003 | Burnside | A61F 2/07 623/1.38 |
| 6,641,607 | B1 * | 11/2003 | Hossainy | A61F 2/91 623/1.15 |
| 2001/0053079 | A1 * | 12/2001 | Demaria | F21V 9/08 362/249.02 |
| 2002/0165601 | A1 * | 11/2002 | Clerc | A61F 2/07 623/1.13 |
| 2003/0055494 | A1 * | 3/2003 | Bezuidenhout | A61F 2/04 623/1.39 |
| 2004/0024456 | A1 * | 2/2004 | Brown, Jr. | A61B 17/0401 623/13.15 |
| 2004/0182511 | A1 * | 9/2004 | Rakos | A61F 2/06 156/287 |
| 2005/0240261 | A1 * | 10/2005 | Rakos | A61F 2/06 623/1.51 |
| 2005/0244455 | A1 * | 11/2005 | Greenawalt | A61F 2/0063 424/423 |
| 2007/0298072 | A1 * | 12/2007 | Kitazono | A61F 2/06 424/426 |
| 2008/0169041 | A1 * | 7/2008 | Nakayama | D04B 1/126 139/387 R |
| 2008/0176206 | A1 * | 7/2008 | Shinoka | A61L 27/3839 435/1.1 |
| 2008/0307765 | A1 * | 12/2008 | Kobayashi | D02G 3/16 57/252 |
| 2010/0094404 | A1 * | 4/2010 | Greenhalgh | A61L 27/34 623/1.15 |
| 2010/0241214 | A1 * | 9/2010 | Holzer | A61F 2/07 623/1.15 |
| 2011/0106115 | A1 * | 5/2011 | Haselby | A61B 5/076 606/151 |
| 2011/0307073 | A1 * | 12/2011 | Teoh | A61F 2/28 623/23.61 |
| 2015/0230953 | A1 * | 8/2015 | Bar | A61F 2/07 623/1.16 |
| 2017/0000928 | A1 | 1/2017 | Onodera et al. | |
| 2018/0289864 | A1 * | 10/2018 | Hagiwara | A61F 2/06 |
| 2019/0231512 | A1 * | 8/2019 | Weber | C08L 67/02 |

FOREIGN PATENT DOCUMENTS

| | | |
|---|---|---|
| CN | 102206888 | 10/2011 |
| JP | S61-288865 | 12/1986 |
| JP | H04-250167 | 9/1992 |
| JP | 2004-313310 | 11/2004 |
| JP | 2010-240200 | 10/2010 |
| JP | 2012-120696 | 6/2012 |
| JP | 2014-014382 | 1/2014 |
| WO | WO 2005/089673 | 9/2005 |
| WO | 2006/054799 | 5/2006 |

OTHER PUBLICATIONS

Onodera, "The Use of Nanomaterials in Regenerative Medicine", Functional Materials (Kino Zairyo (in Japanese with English translation)), 2012, vol. 32, No. 5, pp. 40-48.

Sonoda et al., "Coaxial double-tubular compliant arterial graft prosthesis: time-dependent morphogenesis and compliance changes after implantation", J. Biomed. Mater. Res. A., 2003, vol. 65, No. 2, pp. 170-181.

Extended European Search Report in European Application No. 14871300.1, dated Jul. 18, 2017, 4 pages.

JPO Notification of Reasons for Refusal for JP App No. 2015-553364, dated Aug. 7, 2018 (with English translation) (8 pages).

Office Action in Chinese Patent Application No. 201480067460.4, dated Sep. 20, 2018, 10 pages (English Translation).

Response to Chinese Office Action in Chinese Patent Application No. 201480067460.4, dated Jan. 28, 2019, 4 pages. (English Translation).

Written Amendment filed with the Japanese Patent Office in Japanese Application No. 2015-553364, dated Dec. 3, 2018, 3 pages (with English Translation).

Written Argument filed with the Japanese Patent Office in Japanese Application No. 2015-553364, dated Dec. 3, 2018, 14 pages (with English Translation).

Office Action in Chinese Patent Application No. 201480067460.4, dated Apr. 29, 2019, 5 pages (English Translation only).

Office Action in Korean Patent Application No. 10-2016-7015182, dated Aug. 1, 2019, 2 pages (English Translation only).

Response and Amendment filed in Korean Patent Application No. 10-2016-7015182, dated Sep. 24, 2019, 3 pages (English Translation only).

Response filed in Chinese Patent Application No. 201480067460.4, dated Jul. 12, 2019, 6 pages (English Translation only).

* cited by examiner

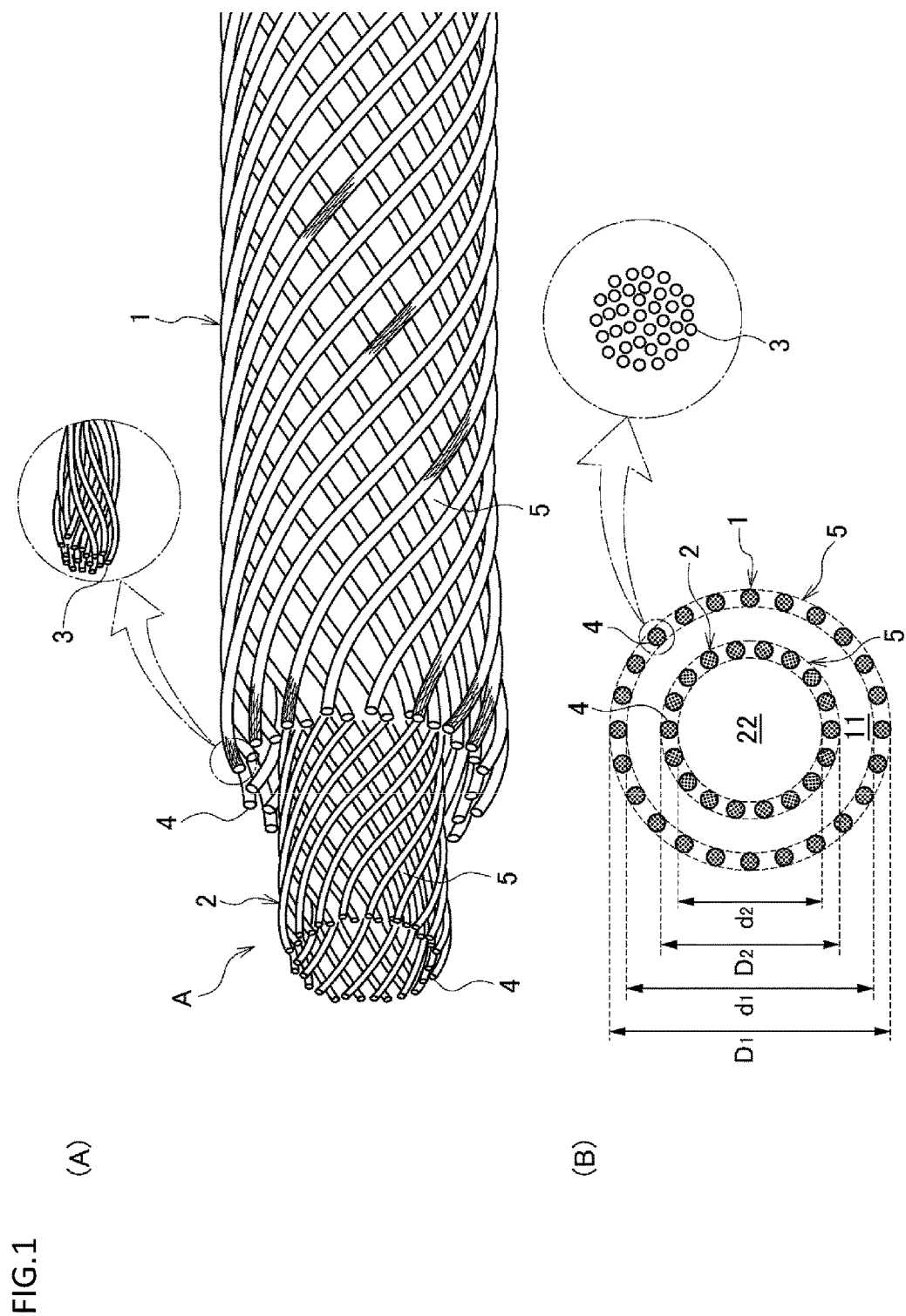

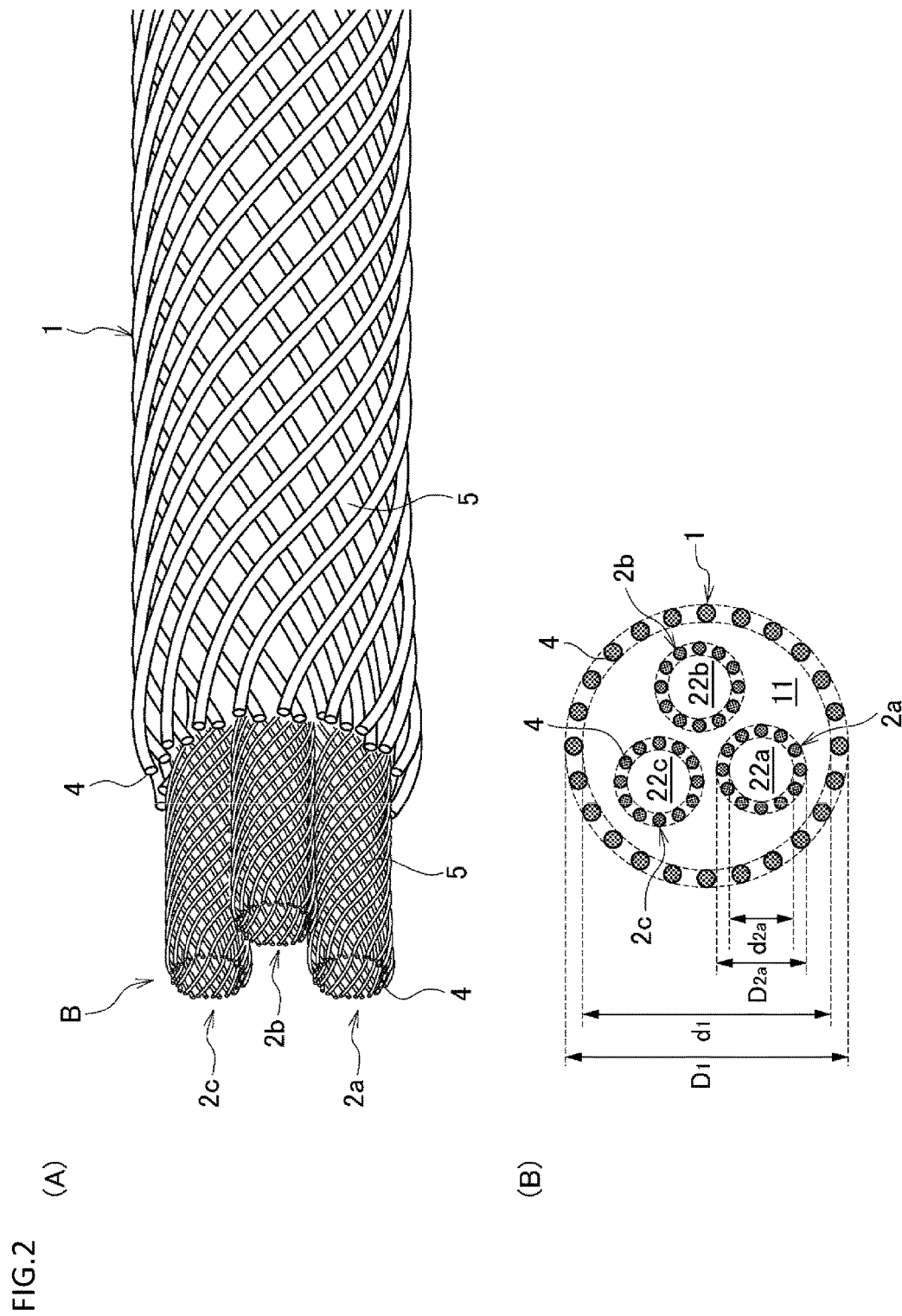

(A)

(B)

(C)

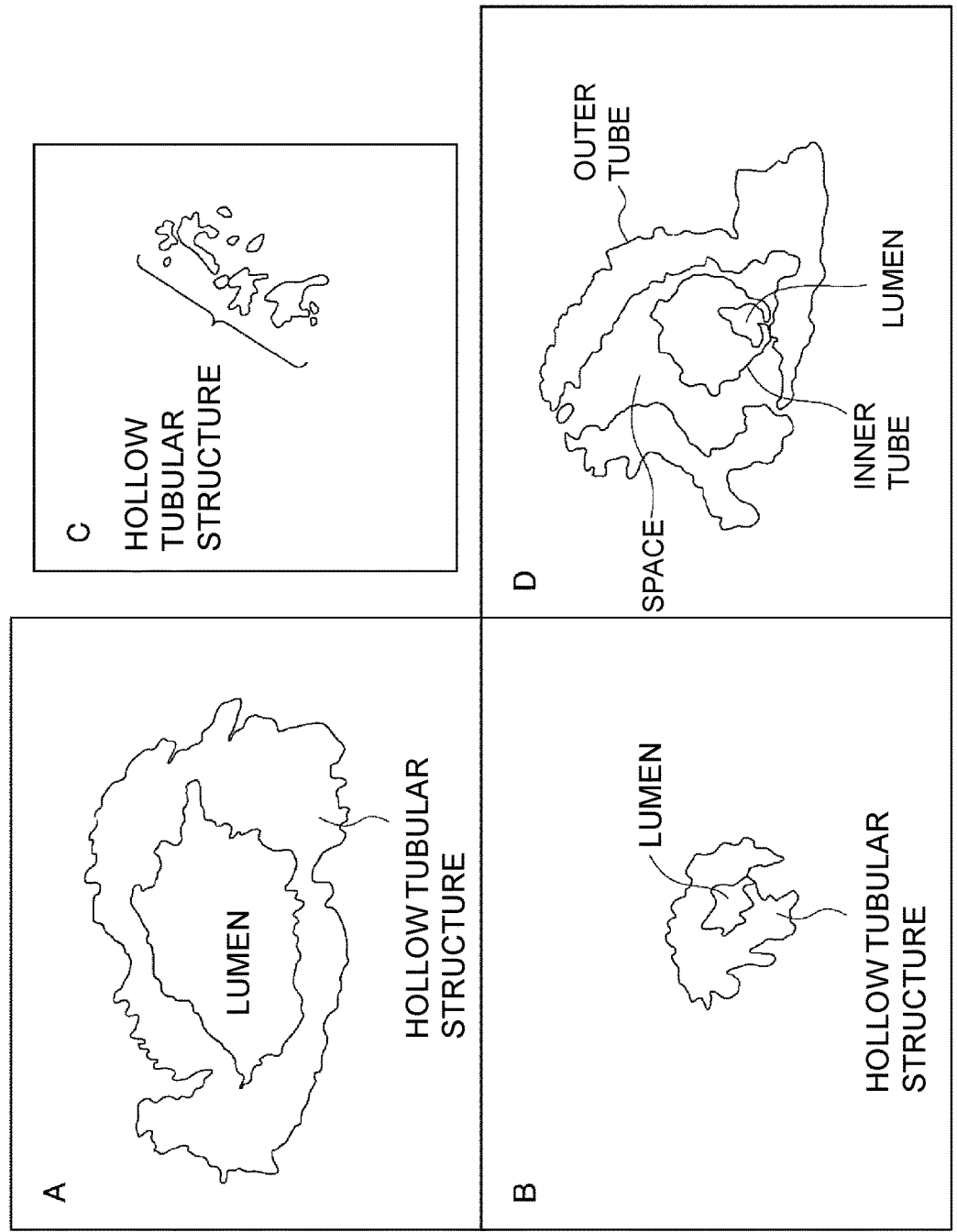

(A)

(B)

(A)

(B)

REVASCULARIZATION GRAFT MATERIAL

TECHNICAL FIELD

The present invention relates to a revascularization graft material.

BACKGROUND ART

Revascularization using graft materials having tubular structure has been attempted in order to treat the vascular disorder due to complication of diabetes, cancer, rheumatism or the like. When a graft material is embedded in a damaged site, a cell inherent to a living body or a cell implanted together with the graft material regenerates the tissue using the graft material as a scaffold, and forms a neovascular vessel.

The graft material is formed of a bioabsorbable material, and is decomposed and absorbed in a living body; however, until the tissue is regenerated after the implantation, the graft material remains at the implantation site without being decomposed, and offers a scaffold and a space for the tissue to be regenerated. The formation of a tubular structure from the graft material can secure the scaffold and the space for such a regenerated tissue in the lumen.

As a graft material having a tubular structure, Patent Literature 1 discloses "a tubular medical material for living tissue regeneration, wherein a first yarn made of a multifilament of a bioabsorbable polymer and a second yarn made of a monofilament of a bioabsorbable polymer are combined and disposed alternately or in an appropriate ratio into a cylinder constituted with a braid-like or tubular knit like tissue" (see claim 1). It is stated that this tubular medical material allows the interior of the cylinder to be a cavity, thus does not disturb the flow of the liquid for regeneration of living tissue, and can prevent the leakage of the liquid inside the lumen (see paragraph 0008 in the aforementioned literature). Patent Literature 1 does not describe the adoption of a multitubular structure for the graft material.

In addition, Non Patent Literature 1 states that "the development of many materials such as polylactic acid and polyglycolic acid as fibrous artificial polymer materials has proceeded, and such materials can also be selected according to applications; a plurality of basic yarns (diameter: 10 μm) of a tissue-dissolution type material were woven to prepare a hollow tube, and various adhesion molecules were bound; setting of a knitting machine allows scaffolds having shapes of many different sizes and shapes to be constructed." (p. 46, left column, lines 6 to 2 from the bottom, in the aforementioned literature). Moreover, it is stated that "the present method has been proved to be a method effective for neural circuit reconstruction in such a limited space as cerebrospinal" (p. 47, left column, lines 15 to 17, in the aforementioned literature); however, it has not been stated that the method can be applied to blood vessels.

Moreover, with respect to a scaffold material for revascularization, Patent Literature 2 discloses a scaffold material which is a hollow cylinder formed of a plurality of concentric layers, and a cylinder formed of aliphatic polyester fiber. The scaffold material is a cylinder formed of a plurality of layers, prepared by winding the fibers obtained by spinning a dope including an aliphatic polyester with an electrospinning method, and is regarded as a material having a structure similar to the structure of blood vessels and a mechanical strength comparable to the mechanical strength of blood vessels (see, p. 2, lines 15 to 22, in the aforementioned literature). In the scaffold material, the plurality of layers are mimetic to the vascular intima, media and adventitia of the actual blood vessel tissue (see, p. 7, lines 1 to 12, ibidem), and the layers are regarded as adhering to each other.

CITATION LIST

Patent Literature

Patent Literature 1: Japanese Patent Laid-Open No. 2010-240200
Patent Literature 2: International Publication No. WO 2006/054799

Non Patent Literature

Non Patent Literature 1: Functional Materials (Kino Zairyo (in Japanese)) Vol. 32, No. 5, May 2012

SUMMARY OF INVENTION

Technical Problem

When a graft material having a tubular structure is embedded in a living body, the graft material is deformed and the lumen is sometimes occluded. In particular, deformation (kinking) tends to occur when a graft material is embedded in a muscle of the thigh or the like in the treatment of diabetic macroangiopathy. When a lumen is occluded due to the deformation of the graft material, the space for tissue regeneration cannot be secured, the migration of cells in the lumen, and the flows of oxygen, blood and extracellular fluid are impeded, and revascularization is liable to be made difficult.

The tubular medical material described in aforementioned Patent Literature 1 improves the kinking resistance of the cylinder by use of a second yarn formed of a thick monofilament (see, paragraph 0008, in the aforementioned literature). The scaffold material described in Patent Literature 2 is regarded to enhance the mechanical strength of a cylinder on the basis of the laminate structure formed of a plurality of layers.

An object of the present invention is to provide a graft material capable of securing a sufficient space for regenerated tissue in the implantation site, and thereby promoting the regeneration of a blood vessel.

Solution to Problem

In order to solve the aforementioned problems, the present invention provides a revascularization graft material comprising an outer tube and an inner tube each being formed by knitting twisted yarns of biodegradable single yarns into a hollow tubular structure, wherein there is provided, in the lumen of the outer tube, at least one inner tube having an outer diameter smaller than the lumen diameter of the outer tube. Because the inner tube functions as a core material for the outer tube, the revascularization graft material is excellent in kinking resistance, and the occlusion of the lumen hardly occurs.

In addition, the revascularization graft material according to the present invention is provided, in the lumen of the outer tube, with a space formed of the lumen internal surface of the outer tube and the external surface of the inner tube. The space serves as a space for tissue regeneration, and also functions to maintain the lumen of the inner tube, through alleviating the deformation of the outer tube and preventing the deformation of the inner tube when the outer tube is deformed by being subjected to external force.

Moreover, the revascularization graft material according to the present invention is provided with, in the outer tube and the inner tube, voids being formed between the knitted twisted yarns and allowing the exterior and the interior of the lumen to communicate with each other. The revascularization graft material allows cells, oxygen, blood and extracellular fluid to move inside and outside of the lumens of the outer tube and the inner tube by passing through the voids of the walls of the regeneration graft material.

The revascularization graft material according to the present invention is allowed to include, as bound to the outer tube and/or the inner tube, one or more factors selected from the group consisting of vascular endothelial growth factor (VEGF), platelet-derived growth factor (PDGF), fibroblast growth factor (FGF) and/or hepatocyte growth factor (HGF). In this case, one or more factors selected from the group may be bound to the outer tube, and one or more other factors selected from the group may be bound to the inner tube.

In the revascularization graft material according to the present invention, vascular cells and/or cells to differentiate into vascular cells may be packed in the lumen of the inner tube and/or the space.

Advantageous Effects of Invention

The present invention provides a graft material excellent in kinking resistance in the implantation site, and capable of securing a sufficient space for the regenerated tissue in the implantation site and thereby promoting the regeneration of a blood vessel.

BRIEF DESCRIPTION OF DRAWINGS

FIG. 1 is a schematic diagram illustrating the revascularization graft material according to a first embodiment of the present invention, FIG. 1(A) and FIG. 1(B) showing a side view and a cross-sectional view of the graft material concerned, respectively.

FIG. 2 is a schematic diagram illustrating the revascularization graft material according to a second embodiment of the present invention, FIG. 2(A) and FIG. 2(B) showing a side view and a cross-sectional view of the graft material concerned, respectively.

FIG. 5-1 is a photograph showing the results of transferring a gene into a cultured cell by using a hollow tubular structure having a gene transfer vector bound thereto.

FIG. 5-2 is a schematic diagram of the photograph shown in FIG. 5-1.

FIG. 6-1 is photographs showing the results (3 days after implantation) of the implantation of a revascularization graft material into a muscle.

FIG. 6-2 is schematic diagrams of the photographs shown in FIG. 6-1.

DESCRIPTION OF EMBODIMENTS

Hereinafter, preferred embodiments for implementing the present invention are described with reference to the accompanying drawings. It is to be noted that the embodiments to be described below are each an example of the representative embodiments of the present invention, and the scope of the present invention is not thereby interpreted narrowly. In addition, examples of the animal species described in the below-described embodiments include, without being limited to, human.

1. Revascularization Graft Material According to First Embodiment

Figures 1, 5:
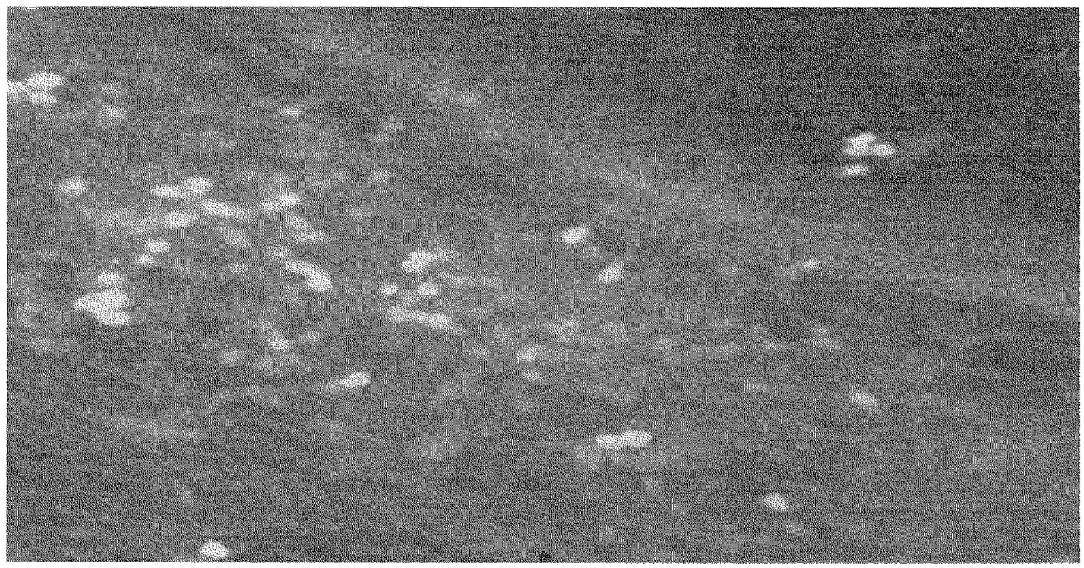

FIG. 1 is a schematic diagram illustrating the revascularization graft material according to the first embodiment of the present invention. The revascularization graft material A is composed of an outer tube 1 and an inner tube 2. The outer tube 1 and the inner tube 2 are each being formed by knitting twisted yarns 4 of biodegradable single yarns 3 into a hollow tubular structure.

[Twisted Yarn of Biodegradable Single Yarn]

The biodegradable single yarn 3 is formed of a natural or synthetic polymer (biodegradable polymer) capable of being hydrolyzed by the action of an enzyme in a living body. The biodegradable polymer is dissolved and absorbed in the living body, and accordingly allows the risk of foreign body reaction to be suppressed to a minimum, and is excellent in safety.

Examples of the biodegradable polymer may include polyglycolic acid, polylactic acid, glycolic acid/lactic acid copolymer, poly-ε-caprolactone, lactic acid/ε-caprolactone copolymer, polyhydroxybutyric acid, gelatin, cross-linked gelatin, collagen, alginic acid, chitin, chitosan, hyaluronic acid, cellulose, starch, polyaspartic acid, polyglutamic acid, and polylysine. The biodegradable polymer is particularly preferably polyglycolic acid, polylactic acid, and glycolic acid/lactic acid copolymer.

The diameter of the biodegradable single yarn 3 can be appropriately selected according to the properties and the damage degree of the tissue into which the graft material is to be inserted. The diameter of the single yarn may be, for example, 200 or less, 100 μm or less, or 10 μm or less. The diameter of the single yarn is regarded to be preferably 1 to 100 μm, more preferably 5 to 50 μm, and furthermore preferably about 10 to about 20 μm.

The cross-sectional shape of the biodegradable single yarn 3 is not particularly limited, and may be, for example, circular or polygonal. The biodegradable single yarn 3 may have protrusions or fine irregularities.

The twisted yarn 4 is formed by twisting a plurality of the biodegradable single yarns 3. In the twisted yarn 4, a plurality of types of biodegradable single yarns 3 different from each other in, for example, materials, diameter and cross-sectional shape may be used in combination. The number of the biodegradable single yarns 3 bundled as the twisted yarn 4 is not particularly limited, and is regarded as 2 to 1000, preferably about 4 to about 500, and particularly preferably about 4 to about 100. The biodegradable single yarn 3 and the twisted yarn 4 used in the outer tube 1 and the biodegradable single yarn 3 and the twisted yarn 4 used in the inner tube 2 are respectively marked with the same symbols, but may be respectively different from each other in, for example, materials, diameter, cross-sectional shape and number of yarns.

In addition, the biodegradable single yarn 3 itself may be a hollow yarn having a hollow structure (tubular structure). Moreover, in the biodegradable single yarn 3, a shape memory material may also be used.

The outer tube 1 and the inner tube 2 are each formed by knitting the twisted yarn 4 into a hollow tubular structure. Specifically, the outer tube 1 and the inner tube 2 each having a hollow structure can be obtained by knitting the twisted yarn 4 around a core such as a metal wire, a resin wire or a fiber, and by finally extracting the core. It is to be noted that the material of the core is not limited to the aforementioned metal, resin and fiber.

In addition, in the obtained outer tube 1 and inner tube 2, the voids 5 derived from the knitted loop structure of the twisted yarn 4 are formed between the twisted yarns 4. The voids 5 allow the exterior and the interior of the lumen of the outer tube 1 (or the inner tube 2) to communicate with each other, and serve as the moving paths for the cells, oxygen, blood and extracellular fluid to move inside and outside of the lumen.

The rigidity of each of the outer tube 1 and the inner tube 2, and the shape and size of the voids 5 can be varied by regulating the materials, diameter, cross-sectional shape and the number of yarns used of the biodegradable single yarn 3, and by regulating, for example, the knit pattern of the twisted yarn 4 and the force applied to the twisted yarn 4 during knitting.

The voids 5 is designed to have a size allowing the cells, oxygen, blood and extracellular fluid to pass therethrough, and thus, the size is, for example, about 5 μm to about 2000 μm. The size of the voids 5 is preferably about 10 μm to about 1000 μm, and more preferably about 100 μm to about 500 μm. The voids 5 of the outer tube 1 and the voids 5 of the inner tube 2 are marked with the same symbol, but may be different from each other in shape and size.

[Multitubular Structure]

The revascularization graft material according to the present invention has a multitubular structure provided with at least one inner tube 2 in the lumen of the outer tube 1. The revascularization graft material A of the present embodiment is designed to have a double-tube structure provided with one inner tube 2 in the lumen of the outer tube 1.

The inner tube 2 has an outer diameter $D_2$ smaller than the lumen diameter $d_1$ of the outer tube 1. The outer diameter $D_2$ of the inner tube 2 is designed to be, for example, about 90%, 80%, 70%, 60%, 50%, 40%, 30%, 20% or 10% of the lumen diameter $d_1$ of the outer tube 1.

The double-tube structure can be prepared by the following procedure. First, the twisted yarn 4 is knitted around a core to prepare the outer tube 1. Next, the inner tube 2 is prepared by knitting the twisted yarn 4 around a core having a diameter smaller than the diameter of the core used for the preparation of the outer tube 1. Then, the inner tube 2 is inserted, together with the core, into the lumen of the outer tube 1 after extracting the core. Finally, the core of the inner tube 2 is extracted, and thus, the revascularization graft material A having a double-tube structure is obtained. The diameters of the cores used may be appropriately set according to the lumen diameter $d_1$ of the outer tube 1 and the lumen diameter $d_2$ of the inner tube 2.

The outer diameter $D_1$ of the outer tube 1 can be appropriately selected according to the properties and the damage degree of the tissue into which the graft material is to be inserted. The outer diameter $D_1$ is possible up to 10000 μm. In the case where the graft material is implanted into an organ such as spinal cord or subcutaneous tissue lack of motility, even the lumen diameter $d_1$ of the outer tube 1 of about 100 μm does not cause the occlusion of the lumen after the implantation. On the other hand, in the case where the graft material is implanted into an organ undergoing active contraction movement such as a muscle, the lumen diameter $d_1$ of about 100 μm liable to cause the occlusion of the lumen, and accordingly the lumen diameter $d_1$ is desirably designed to be about 500 μm. In consideration of the adaptability to human, a lumen diameter $d_1$ designed to be relatively large is useful for the circulation dynamics improvement effect and the prevention of the lumen occlusion.

The following numerical values are quoted as a set of examples of the diameters of the outer tube 1 and a set of examples of the diameters of the inner tube 2.

Outer tube 1: Outer diameter $D_1$: 600 μm, lumen diameter $d_1$: 500 μm

Inner tube 2: Outer diameter $D_2$: 300 μm, lumen diameter $d_2$: 200 μm

The length of the revascularization graft material A is designed to be about 2 mm to about 100 cm, and preferably about 1 cm to about 30 cm.

The revascularization graft material A is provided, in the lumen of the outer tube 1, with a space 11 formed with the lumen internal surface of the outer tube 1 and the external surface of the inner tube 2. The space 11 serves as a space for tissue regeneration due to the cell inherent to a living body or the cells implanted together with the graft material. The size of the space 11 allowing a space for tissue regeneration to be secured is enough and is not otherwise particularly limited; the size of the space 11 is appropriately designed according to the properties and the damage degree of the tissue into which the graft material is to be inserted.

The revascularization graft material A has a double-tube structure (or multitubular structure), and the inner tube 2 functions as the core material for the outer tube 1; accordingly, the revascularization graft material A is excellent in kinking resistance, and even in the case where the graft material is implanted into an organ undergoing active contraction movement such as a muscle, the lumen of the outer tube 1 and the lumen of the inner tube 2 are hardly occluded. In addition, granted that the outer tube 1 is deformed by being subjected to external force, the space 11 alleviates the deformation of the outer tube 1 and prevents the deformation of the inner tube 2, and accordingly the lumen (see reference No. 22 in FIG. 1(B)) of the inner tube 2 can be maintained. Accordingly, in the revascularization graft material A, a sufficient space for the regenerated tissue is secured in the implantation site, the migration of cells and the flows of oxygen, blood and extracellular fluid in the space concerned are promoted, and thus the regeneration of a blood vessel can be effectively induced. More specifically, the migratory cells entering from the tissue into the lumen of the outer tube 1 and the lumen of the inner tube 2 and the implanted cells packed in the lumens can grow along the space 11 and the lumen 22 of the inner tube 2, without being disturbed by the cells of the host, and accordingly the extension of the neovascular vessel is promoted.

Moreover, in the revascularization graft material A, because the outer tube 1 and the inner tube 2 have the voids 5, the movement of cells, oxygen, blood and extracellular fluid inside and outside of the lumen of the outer tube 1 and the lumen of the inner tube 2 is made possible. Accordingly, in the revascularization graft material A, the migratory cells and the tissue fluid in the tissue can pass through the voids 5 to enter the lumens, and the implanted cells packed in the lumens can pass through the voids 5 to leave the lumens and enter the tissue. The implanted cells leaving the lumen of the revascularization graft material A and entering the tissue move to the implantation site and the periphery thereof to contribute to the vascular reconstruction.

[Adhesion Molecule]

A cell adhesion molecule may be bound to the revascularization graft material A. The cell adhesion molecule means a molecule to promote the adhesion of cells, and examples of the cell adhesion molecule include laminin, fibronectin, collagen, polylysine and polyornithine.

To the revascularization graft material A, two or more types of cell adhesion molecules may be bound in combination. In addition, different types of cell adhesion molecules may be bound to the respective sites of the revascularization graft material A. For example, by binding different types of cell adhesion molecules to the outer tube 1 and the inner tube 2, respectively, or by binding different types of cell adhesion molecules to an end and the central portion of the revascularization graft material A, respectively, it is possible to prepare a revascularization graft material A having intended cell adhesion properties in compliance with the cells present in the tissue into which a graft material is to be inserted and the cells to be implanted together with the revascularization graft material A.

The binding of the cell adhesion molecule to the revascularization graft material A may be based on either chemical binding or physical binding (for example, adsorption). For example, a revascularization graft material A to which laminin is bound is obtained by immersing a revascularization graft material A in an aqueous laminin solution (1 to 1000 μg/ml) at room temperature for 2 to 16 hours, washing the revascularization graft material A with distilled water and drying the revascularization graft material A.

[Growth Factor]

To the revascularization graft material A, heparin and/or heparan sulfate may be bound. Heparin and heparan sulfate have binding affinity to the virus used as the gene transfer vector such as adeno-associated virus. Accordingly, by binding heparin or the like to the revascularization graft material A, a virus vector can be bound to the revascularization graft material A through the intermediary of heparin or the like. As the virus vector, sendaivirus vector, lentivirus vector, retrovirus vector, adenovirus vector and the like can also be used.

Examples of the virus vector include: virus vectors expressing factors having an action to promote the growth/maturation of neovascular vessels such as vascular endothelial growth factor (VEGF), platelet-derived growth factor (PDGF), fibroblast growth factor (FGF/bFGF) and hepatocyte growth factor (HGF).

In addition, heparin and heparan sulfate also have binding affinity to many trophic factors such as VEGF, HGF, FGF/bFGF, epidermal growth factor (EGF), chemokine and midkine. Accordingly, by binding heparin or the like to the revascularization graft material A, a trophic factor having heparin binding property can also be bound to the revascularization graft material A. Moreover, the proteins of these factors can also be directly bound to the revascularization graft material A without intermediary of heparin.

For the means for introducing and expressing the factors having an action to promote the growth/maturation of neovascular vessels such as VEGF, heretofore known gene vectors such as plasmid can also be adopted, without being limited to the aforementioned virus vectors. As the means for expressing the factors involved in blood vessel formation, it is also possible to use DNA (inclusive of sense strand and antisense strand) and RNA (inclusive of sense strand, antisense strand, siRNA and miRNA). For example, when the sense strand is used, it is possible to induce the expression of the factor involved in the blood vessel formation. When the antisense strand is used or when RNAi is used, it is considered to induce the expression of the factor involved in the blood vessel formation by suppressing the expression of the transcription factor functioning in the suppression of the expression of the factor involved in the blood vessel formation. Because an amino group-containing compound such as aforementioned polylysine forms an ionic bond with nucleic acids such as DNA and RNA, when polylysine is bound as a cell adhesion molecule to the revascularization graft material A, it is also possible to bind to the revascularization graft material A, a nucleic acid to control the expression of the gene involved in blood vessel formation, through the intermediary of polylysine. In the present invention, the mode and the binding form of the growth factor binding to the revascularization graft material may be any mode and any binding form that allow the growth factor to display the function thereof; as described above, a mode of a nucleic acid or a mode of a protein may be adopted; the binding of these may take a form through the intermediary of heparin and/or heparan sulfate; moreover, when the factor is a nucleic acid, the mode of the nucleic acid itself or the mode of being mounted on a gene vector may be adopted.

One or more of the aforementioned factors may be bound to each of the outer tube 1 and the inner tube 2, or alternatively, different factors may be bound to the outer tube 1 and the inner tube 2, respectively. The combination of the factors respectively bound to the outer tube 1 and the inner tube 2 can be appropriately set according to the properties and the damage degree of the tissue into which the graft material is to be inserted.

As an example, an environment close to the blood vessels in a living body can be reproduced by binding VEGF to induce and proliferate the vascular endothelial cells to the inner tube 2, and by binding other blood vessel formation-related factors (such as HGF, FGF2 and PDGF) to the outer tube 1. Alternatively, in another possible case, VEGF is bound to the outer tube 1 and other blood vessel formation-related factors (such as HGF, FGF2 and PDGF) are bound to the inner tube 2. The construction of the environment, in the implantation site, close to the blood vessels in a living body with the revascularization graft material A can effectively promote the regeneration of blood vessels as compared with conventional methods merely injecting, for example, VEGF into the tissue.

[Cells]

In the space 11 and the lumen 22 of the inner tube 2, vascular cells and/or cells to be differentiated into vascular cells may also be packed. The "vascular cells" as referred to herein include at least the vascular endothelial cell and the vascular pericyte (pericyte). The "cells to be differentiated into vascular cells" include, for example, precursor cells of vascular endothelial cell and pericyte; stem cells such as induced pluripotent stem cell (iPS cell) and embryonic stem cell (ES cell); and mesenchymal stem cell.

Moreover, when cardiac myocytes are packed together with vascular cells in the space 11 and the lumen 22 of the inner tube 2, the application to the treatment of myocardial infarction and cardiomyopathy is possible. Moreover, implanted cells may also be packed in the lumen 22 of the inner tube 2, and factors promoting the growth/maturation of neovascular vessels such as VEGF, PDGF, FGF/bFGF and HGF may also be bound in the space 11. In this way, the construction of the blood vessel structure with, for example, implanted vascular endothelial cells can be promoted.

In place of cells, or together with cells, various trophic factors and various drugs may be introduced into the space 11 and the lumen 22 of the inner tube 2. When gelled trophic factors and gelled drugs are packed in the space 11 and the lumen 22 of the inner tube 2, these substances can be released in the implantation site over a long term.

[Magnetic Body]

A magnetic body may be connected to the revascularization graft material A. By connecting a magnetic body to the revascularization graft material A, the revascularization graft material A can be induced to and made to indwell in the target site in the tissue by using a magnetic field generator.

As the materials for the magnetic body, it is possible to use any metal materials such as iron, nickel, cobalt and the alloys of these (such as iron-chromium-cobalt alloy and aluminum-nickel-cobalt alloy); ferrite; rare earth magnets; and magnetic stainless steels. Examples of the rare earth magnet include a samarium-cobalt (SmCo) magnet and a neodymium (NdFeB) magnet. For the magnetic body, these metal materials coated with the materials having biocompatibility and heretofore used for coating syringe needles or the like may be used. Examples of the biocompatible materials include Parylene (Registered Trademark) as a paraxylylene polymer, silicon, polypropylene and tetrafluoroethylene. When an iron-chromium-cobalt alloy (FeCrCo) is used as the metal material, a nanowire prepared by thermally extending a commercially available FeCrCo wire can be used.

The magnetic body may be connected to an end of the revascularization graft material A, or may be fixed in a state of being at least partially inserted in the lumen of the revascularization graft material A.

In order to connect the magnetic body to an end of the revascularization graft material A, one end of the magnetic body and one end of the revascularization graft material A are bound to each other with a paste or by thermal fusion bonding. By one-spot binding of the magnetic body and the revascularization graft material A, the magnetic body and the revascularization graft material A can be simultaneously controlled by external magnetic field. As a paste, for example, a paste prepared by mixing polylactic acid (PLLA) with chloroform in a concentration of 0.5% can be used. In the case of thermal fusion bonding, fusion bonding may be performed by applying a soldering iron at about 200° C. to the revascularization graft material A. It is a possible method to mechanically bind one end of the magnetic body to one end of the revascularization graft material A.

In order to fix the magnetic body in a state of being at least partially inserted in the lumen of the revascularization graft material A, the magnetic body is inserted in the lumen of the revascularization graft material A, and the revascularization graft material A is heated at about 200° C. for a few seconds to melt the yarns, and made to adhere to the magnetic body. Alternatively, the adhesion may also be performed with a chemical.

In order to facilitate the induction and the insertion into the tissue of the magnetic body with a magnetic field generator, it is preferable to form the magnetic body in a thin needle or rod shape. The needle-shaped or rod-shaped magnetic body (hereinafter referred to as "the needle-shaped magnetic body") is preferably an ultra fine magnet. By making the magnetic body ultra fine, the bleeding or the damage of the tissue caused by the insertion or the indwelling of the revascularization graft material A can be suppressed to the minimum.

The diameter of the needle-shaped magnetic body can be appropriately selected according to the properties and the damage degree of the tissue into which the graft material is to be inserted, and is set to be, for example, 200 µm or less, preferably 100 µm or less and more preferably 10 µm or less. The diameter of the needle-shaped magnetic body is desirably smaller than the outer diameter of the revascularization graft material A. The length of the needle-shaped magnetic body can also be appropriately selected according to the properties and the damage degree of the tissue into which the graft material is to be inserted.

As the magnetic field generator, for example, the magnetic field generator disclosed in International Publication No. WO2001/061474 can be used. The magnetic field generator is equipped with an electromagnet and a controller to control the generated magnetic field, and has a induction needle at a tip. The induction needle is magnetic metal needle for enhancing the magnetic flux density of the magnetic field generated from the electromagnet. After the induction needle is brought into close contact with or inserted into the vicinity of the tissue into which the revascularization graft material A is to be inserted, the magnetic field is generated by operating the controller. By regulating the magnetic field strength and the position of the induction needle, the magnetic body is guided and thus, the revascularization graft material A can be inserted and made to indwell at the intended position in the tissue.

In this case, by using a high sensitivity magnetic sensor, the accurate position of the magnetic body can be monitored. As the monitoring method during surgery using a high sensitivity magnetic sensor, for example, possible are the methods using a Hall element, a MI (magnetic impedance) sensor, and a SQUID (superconducting quantum interference device) sensor.

2. Revascularization Graft Material According to Second Embodiment

Figures 2, 5:
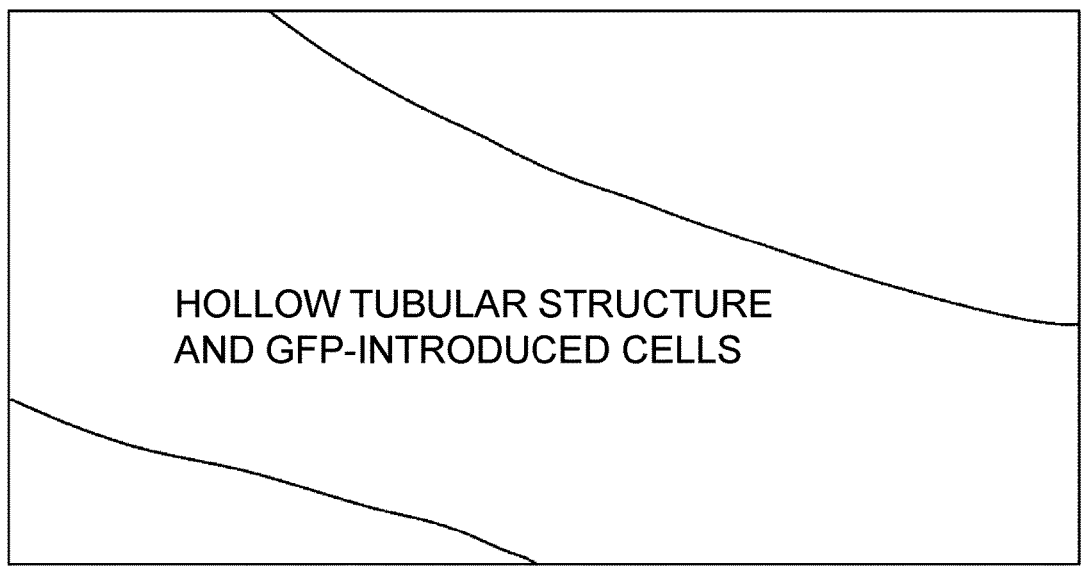

FIG. 2 is a schematic diagram illustrating the revascularization graft material according to the second embodiment of the present invention. The revascularization graft material B is different from the aforementioned revascularization graft material A in that a plurality of inner tubes are provided in the lumen of the outer tube 1. Specifically, the revascularization graft material B of the present embodiment is designed to have a multitubular structure in which three inner tubes 2a, 2b and 2c are provided in the lumen of the outer tube 1. It is to be noted that the number of the inner tubes provided in the lumen of the outer tube 1 may be 2 or 4 or more.

The twisted yarn 4 (and the biodegradable single yarn 3) constituting the revascularization graft material B, the hollow tubular structures, the voids 5 and the like of the outer tube 1 and the inner tubes 2a, 2b and 2c are the same as those of the revascularization graft material A, and accordingly detailed description of the revascularization graft material B is omitted.

The inner tube 2a has an outer diameter $D_{2a}$ smaller than the lumen diameter $d_1$ of the outer tube 1. The outer diameter $D_{2a}$ of the inner tube 2a is designed to be, for example, about 70%, 60%, 50%, 40%, 30%, 20%, 10% or 5% of the lumen diameter $d_1$ of the outer tube 1. The outer diameters of the inner tubes 2b and 2c are the same as the outer diameter of the inner tube 2a, but the outer diameters of the inner tubes 2a, 2b and 2c may be identical or different from each other.

The multitubular structure can be prepared by the following procedure. First, the twisted yarn 4 is knitted around a core to prepare the outer tube 1. Next, the inner tubes 2a, 2b and 2c are each prepared by knitting the twisted yarn 4 around a core having a diameter smaller than the diameter of the core used for the preparation of the outer tube 1. Then, the inner tubes 2a, 2b and 2c are each inserted, together with the core, into the lumen of the outer tube 1 after extracting the core. Finally, the cores of the inner tubes 2a, 2b and 2c are successively extracted, and thus, the revascularization graft material B having a multitubular structure is obtained. The diameters of the cores used may be appropriately set according to the lumen diameter $d_1$ of the outer tube 1 and the lumen diameter $d_{2a}$ of the inner tube 2a (and the lumen diameters of the inner tubes 2b and 2c). Similarly, two or four or more inner tubes can also be provided.

The following numerical values are quoted as a set of examples of the outer and lumen diameters of the outer tube 1 and a set of examples of the outer and lumen diameters of the inner tube 2a (and the inner tubes 2b and 2c).

Outer tube 1: Outer diameter $D_1$: 600 μm, lumen diameter $d_1$: 500 μm

Inner tube 2a: Outer diameter $D_{2a}$: 200 μm, lumen diameter $d_{2a}$: 100

The revascularization graft material B is provided, in the lumen of the outer tube 1, with a space 11 formed with the lumen internal surface of the outer tube 1 and the external surfaces of the inner tubes 2a, 2b and 2c. The space 11 serves as a space for tissue regeneration due to the cell inherent to a living body or the cells implanted together with the graft material.

The revascularization graft material B has a multitubular structure, and the inner tubes 2a, 2b and 2c function as the core materials for the outer tube 1; accordingly, the revascularization graft material B is excellent in kinking resistance, and even in the case where the graft material is implanted into an organ undergoing active contraction movement such as a muscle, the lumen of the outer tube 1 and the lumens of the inner tubes 2a, 2b and 2c are hardly occluded. The revascularization graft material B has the plurality of the inner tubes provided in the lumen of the outer tube 1, and thus acquires a higher kinking resistance as compared with the kinking resistance of the aforementioned revascularization graft material A.

In addition, granted that the outer tube 1 is deformed by being subjected to external force, the space 11 alleviates the deformation of the outer tube 1 and prevents the deformation of the inner tubes 2a, 2b and 2c, and accordingly the lumens (see reference Nos. 22a, 22b and 22c in FIG. 2(B)) of the inner tubes 2a, 2b and 2c can be maintained. Accordingly, in the revascularization graft material B, a sufficient space for the regenerated tissue is secured in the implantation site, the migration of cells and the flows of oxygen, blood and extracellular fluid in the space concerned are promoted, and thus the regeneration of a blood vessel can be effectively induced. More specifically, the migratory cells entering from the tissue into the lumen of the outer tube 1 and the lumens of the inner tubes 2a, 2b and 2c and the implanted cells packed in the lumens can grow along the space 11 and the lumens 22a, 22b and 22c of the inner tubes 2a, 2b and 2c without being disturbed by the cells of the host, and accordingly the extension of the neovascular vessel is promoted.

To the revascularization graft material B, the aforementioned cell adhesion molecules, heparin and/or heparan sulfate, growth factor, virus vector and the like may be bound, and if necessary, a magnetic body may also be bound. In this case, different cell adhesion molecules or the like may be bound to the respective inner tubes 2a, 2b and 2c.

In the space 11 and the lumens 22a, 22b and 22c of the inner tubes 2a, 2b and 2c, vascular cells and/or cells to be differentiated into vascular cells may also be packed, and gelled trophic factors and gelled drugs may also be packed. In each of the lumens, cells and/or drugs can be packed in optional combinations. In the revascularization graft material B according to the present embodiment, three inner tubes are provided, and hence it is possible to implement various combinations of the cells and the drugs to be packed in the space 11 and the respective lumens of the inner tubes 2a, 2b and 2c. On the other hand, the aforementioned revascularization graft material A according to the first embodiment can be designed to have the relatively large space 11 and the relatively large lumen 22 of the inner tube 2, and is accordingly suitable for packing and implanting large amounts of cells and drugs.

The combinations of the cells and drugs to be packed in the space 11 and the lumens 22a, 22b and 22c of the inner tube 2a, 2b and 2c can be implemented as follows. In the case where two or four or more inner tubes are provided, various combinations are similarly possible.

TABLE 1

| | Combination example A | Combination example B | Combination example C | Combination example D |
|---|---|---|---|---|
| Space 11 | Nothing | Nothing | Nothing | Drug 1 |
| Lumen 22a | Nothing | Nothing | Nothing | Nothing |
| Lumen 22b | Drug 1 | Cell 1 | Drug 1 | Drug 2 |
| Lumen 22c | Cell 1 | Cell 2 | Drug 2 | Cell 1 |

3. Revascularization Graft Material According to Third Embodiment

Figure 3:
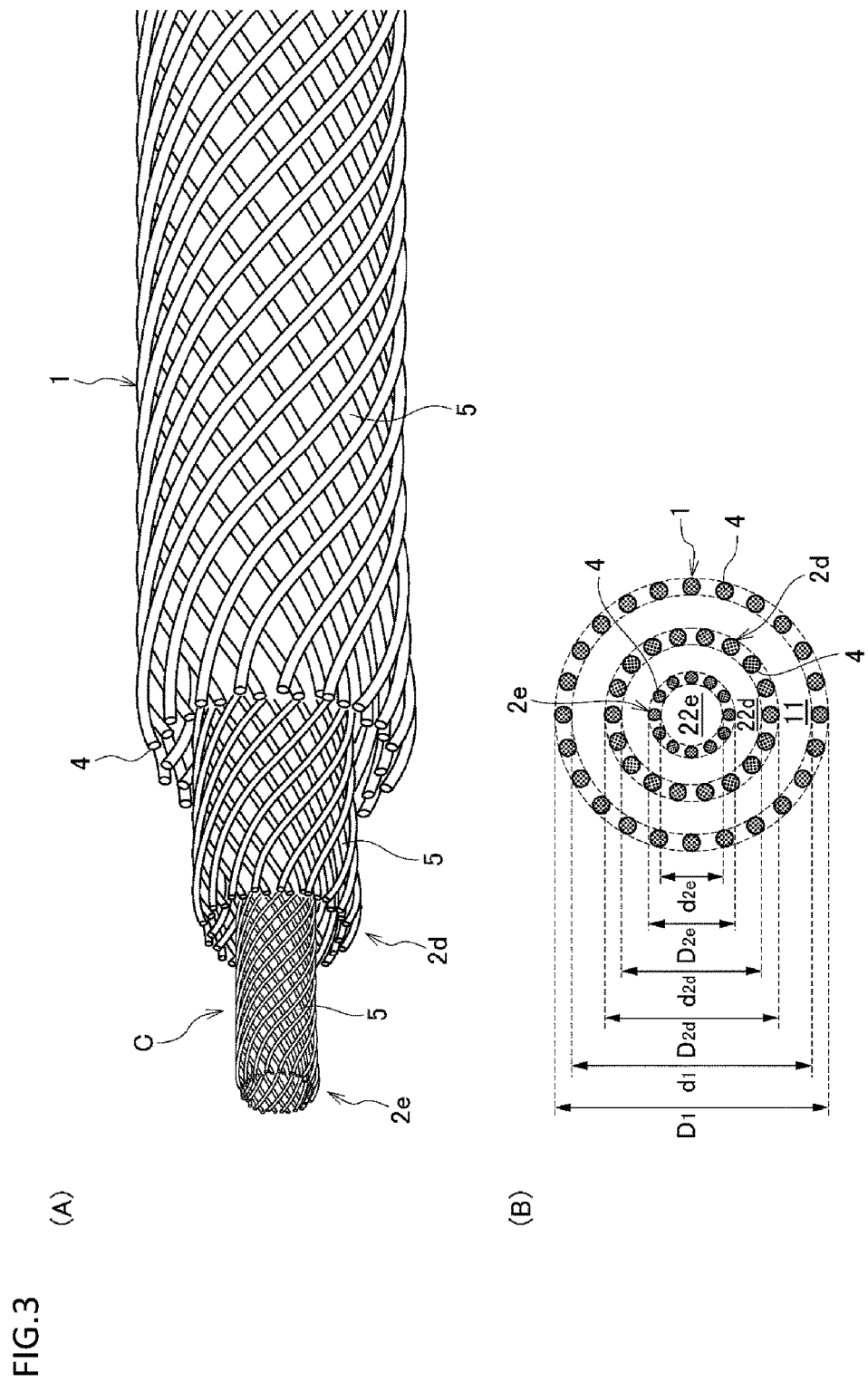
FIG. 3 is a schematic diagram illustrating the revascularization graft material according to a third embodiment of the present invention, FIG. 3(A) and FIG. 3(B) showing a side view and a cross-sectional view of the graft material concerned, respectively.

FIG. 3 is a schematic diagram illustrating the revascularization graft material according to the third embodiment of the present invention. The revascularization graft material C is different from the aforementioned revascularization graft material A in that a second inner tube 2e is further provided in the lumen of a first inner tube 2d provided in the lumen of the outer tube 1. Specifically, in the revascularization graft material C of the present embodiment, the first inner tube 2d is an inner tube in relation to the outer tube 1, and at the same time an outer tube in relation to the second inner tube 2e. The revascularization graft material C has a multitubular structure constituted with three tubular structures (the outer tube 1, the first inner tube 2d, and the second inner tube 2e) forming a "nested" structure. The "nested" structure is not limited to the triple structure shown in the accompanying drawing, and may be a quadruple or higher structure.

The twisted yarn 4 (and the biodegradable single yarn 3) constituting the revascularization graft material C, the hollow tubular structures, the voids 5 and the like of the outer tube 1, the first and second inner tubes 2d and 2e are the same as those of the revascularization graft material A, and accordingly detailed description of the revascularization graft material C is omitted.

The first inner tube 2d has an outer diameter $D_{2d}$ smaller than the lumen diameter $d_1$ of the outer tube 1. In addition, the second inner tube 2e has an outer diameter $D_{2e}$ smaller than the lumen diameter $d_{2d}$ of the first inner tube 2d. The outer diameter $D_{2d}$ of the first inner tube 2d is designed to be, for example, about 90%, 80%, 70%, 60%, 50%, 40%, 30%, 20% or 10% of the lumen diameter $d_1$ of the outer tube 1. Similarly, the outer diameter $D_{2e}$ of the second inner tube 2e is designed to be, for example, about 90%, 80%, 70%, 60%, 50%, 40%, 30%, 20% or 10% of the lumen diameter $d_{2d}$ of the first inner tube 2d.

The multitubular structure can be prepared by the following procedure. First, the twisted yarn 4 is knitted around a core to prepare the outer tube 1. Next, the first inner tube 2d is prepared by knitting the twisted yarn 4 around a core having a diameter smaller than the diameter of the core used for the preparation of the outer tube 1. Additionally, the second inner tube 2e is prepared by knitting the twisted yarn 4 around a core having a diameter smaller than the diameter of the core used for the preparation of the first inner tube 2d. Then, the first inner tube 2d is inserted, together with the core, into the lumen of the outer tube 1 after extracting the core, and then the core for the first inner tube 2d is extracted. Additionally, the second inner tube 2e is inserted, together with the core, into the lumen of the first inner tube 2d after extracting the core, then the core for the second inner tube 2e is extracted, and thus, the revascularization graft material C having a multitubular structure is obtained. The diameters of the cores used may be appropriately set according to the lumen diameter $d_1$ of the outer tube 1 and the lumen diameters $d_{2d}$ and $d_{2e}$ of the first and second inner tubes 2d and 2e. Similarly, a quadruple or higher structure can also be prepared.

The following numerical values are quoted as a set of examples of the outer and lumen diameters of the outer tube 1, a set of examples of the outer and lumen diameters of the first inner tube 2d and a set of examples of the outer and lumen diameters of the second inner tube 2e.

Outer tube 1: Outer diameter $D_1$: 700 μm, lumen diameter $d_1$: 600 μm

First inner tube 2d: Outer diameter $D_{2d}$: 400 μm, lumen diameter $d_{2d}$: 300 μm Second inner tube 2e: Outer diameter $D_{2e}$: 200 μm, lumen diameter $d_{2e}$: 100 μm The revascularization graft material C is provided, in the lumen of the outer tube 1, with a space 11 formed with the lumen internal surface of the outer tube 1 and the external surface of the first inner tube 2d. The revascularization graft material C is also provided, in the lumen of the first inner tube 2d, with a space 22d formed with the lumen internal surface of the first inner tube 2d and the external surface of the second inner tube 2e. These spaces 11 and 22d serve as spaces for tissue regeneration due to the cell inherent to a living body or the cells implanted together with the graft material.

The revascularization graft material C has a multitubular structure, and the first and second inner tubes 2d and 2e function also as the core materials for the outer tube 1; accordingly, the revascularization graft material C is excellent in kinking resistance, and even in the case where the graft material is implanted in an organ undergoing active contraction movement such as a muscle, the lumen of the outer tube 1 and the lumens of the inner tubes 2d and 2e are hardly occluded. The revascularization graft material C has the "nested" multitubular structure, and thus displays a higher kinking resistance as compared with the kinking resistance of the aforementioned revascularization graft material A.

In addition, granted that the outer tube 1 is deformed by being subjected to external force, the space 11 alleviates the deformation of the outer tube 1 and prevents the deformation of the first inner tube 2d, Moreover, granted that even the first inner tube 2d is deformed, the space 22d alleviates the deformation of the first inner tube 2d and prevents the deformation of the second inner tube 2e. Accordingly, the space 22d and the lumen (see the reference No. 22e in FIG. 3(B)) of the second inner tube 2e are maintained. Accordingly, in the revascularization graft material C, sufficient spaces for the regenerated tissue are secured in the implantation site, the migration of cells and the flows of oxygen, blood and extracellular fluid in the spaces concerned are promoted, and thus the regeneration of a blood vessel can be effectively induced. More specifically, the migratory cells entering from the tissue into the lumen of the outer tube 1 and the lumens of the inner tubes 2d and 2e and the implanted cells packed in the lumens can grow along the spaces 11 and 22d, and the lumen 22e of the inner tube 2e without being disturbed by the cells of the host, and accordingly the extension of the neovascular vessel is promoted.

To the revascularization graft material C, the aforementioned cell adhesion molecules, heparin and/or heparan sulfate, growth factor, virus vector and the like may be bound, and if necessary, a magnetic body may also be bound. In this case, different cell adhesion molecules or the like may be bound to the outer tube 1 and the inner tubes 2d and 2e, respectively.

In the spaces 11 and 22d, and the lumen 22e of the second inner tube 2e, vascular cells and/or cells to be differentiated into vascular cells may also be packed, and gelled trophic factors and gelled drugs may also be packed. In each of the lumens, cells and/or drugs can be packed in optional combinations. In the revascularization graft material C according to the present embodiment, three tubular structures (the outer tube 1, the first inner tube 2d, and the second inner tube 2e) are provided so as to form a "nested" structure, and hence it is possible to implement various combinations of the cells and the drugs to be packed in the spaces 11 and 22d, and the lumen 22e of the inner tube 2e.

The combinations of the cells and drugs to be packed in the spaces 11 and 22d, and the lumen 22e of the inner tube 2e can be implemented as follows. In the case where a quadruple or higher structure is adopted, various combinations are also similarly possible.

TABLE 2

|  | Combination example A | Combination example B | Combination example C | Combination example D |
|---|---|---|---|---|
| Space 11 | Nothing | Nothing | Nothing | Drug 1 |
| Space 22d | Drug 1 | Drug 1 | Cell 1 | Cell 1 |
| Lumen 22e | Cell 1 | Drug 2 | Cell 2 | Drug 2 |

Moreover, the revascularization graft material according to the present invention may also have a structure implemented by combining the multitubular structure in the aforementioned second embodiment and the multitubular structure in the third embodiment.

4. Method for Laying Revascularization Graft Material

The method of laying the revascularization graft material according to the present invention may be any one of the following methods: (1) a method in which the whole of the graft material is embedded in subcutaneous tissue and/or muscle; (2) a method in which both ends of the graft material are exposed to the outside of the body, and only the central portion is embedded in subcutaneous tissue and/or muscle; (3) a method in which one end of the graft material is exposed to the outside of the body and the rest of the graft material is embedded in subcutaneous tissue and/or muscle.

[Laying by Magnetism]

When the revascularization graft material according to the present invention is provided with a magnetic body, as described above, the graft material can be guided to and laid in the target site in the tissue by using a magnetic field generator. In this case, by monitoring the position of the magnetic body with a high sensitivity magnetic sensor, the revascularization graft material can be implanted accurately at the target position.

The magnetic body may be made to indwell at the insertion site when a harmless iron body is used; after the magnetic body is guided to the outside of the body, the magnetic body is disconnected from the revascularization graft material, and then only the revascularization graft material may be made to indwell in the body. In consideration of safety, it is preferable to make only the revascularization graft material indwell in the body.

In the case of a structure in which a relatively long needle-shaped magnetic body is inserted into the lumen of the revascularization graft material, it is made possible to insert line of magnetic force over the whole length of the revascularization graft material, and hence a strong magnetic field induction effect is obtained.

[Laying with a Guide Wire]

In addition, the revascularization graft material according to the present invention can be manually inserted into and laid in the tissue without using magnetic field. Whether or not the guide wire reaches the target site can be verified by, for example, X-ray camera radioscopy.

Figure 4:
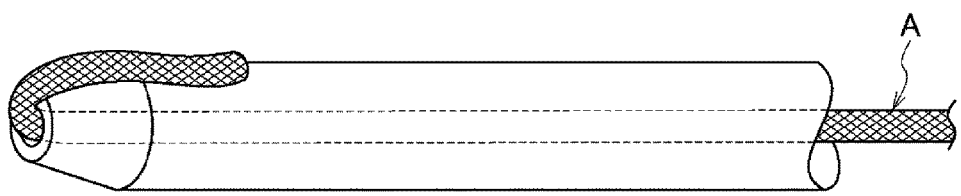
FIG. 4 is a schematic diagram illustrating a guide wire usable for laying the revascularization graft material according to the present invention.
Figure 4:
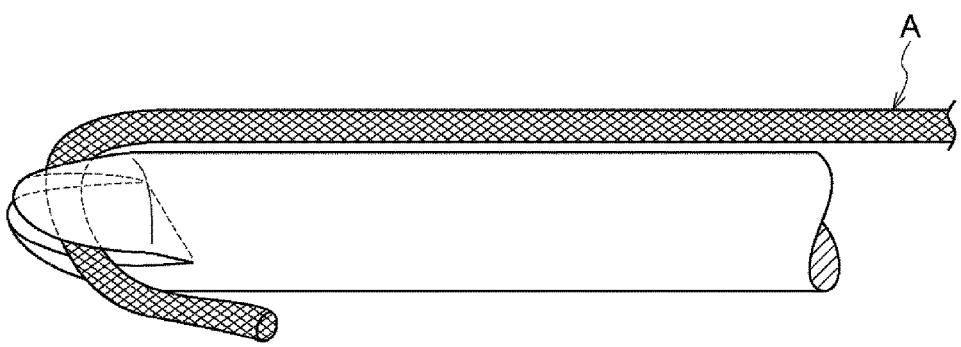
Figure 4:
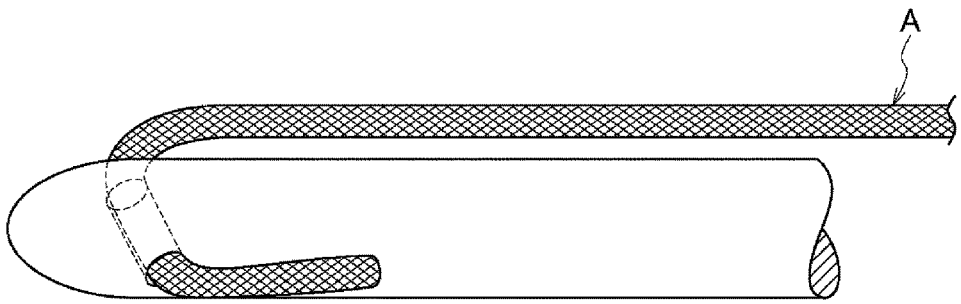

FIG. 4 shows the examples of the guide wires usable for laying the revascularization graft material according to the present invention.

The tubular guide wire shown in FIG. 4(A) is used by allowing the revascularization graft material to pass from the opening at the tip through the tubular guide wire, and is suitable for laying a thick revascularization graft material. The tip is sharp so as for the guide wire to be able to enter into a muscle. The guide wire is compatible with the aforementioned (1) to (3) laying methods. In addition, the guide wire also allows two or more strings of revascularization graft materials to be laid simultaneously.

The guide wire shown in FIG. 4(B) is used by grappling the revascularization graft material with the groove at the tip of the tubular guide wire. The tip is sharp so as for the guide wire to be able to enter into a muscle. The guide wire can lay the revascularization graft material only by allowing the tip of the guide wire to be inserted up to the target site and by subsequently being extracted, and is compatible with the aforementioned (2) and (3) laying methods. In addition, the guide wire also allows two or more strings of revascularization graft materials to be laid simultaneously.

The guide wire shown in FIG. 4(C) is used by allowing the revascularization graft material to pass through the hole at the tip of the guide wire. The tip is sharp so as for the guide wire to be able to enter into a muscle. The guide wire is compatible with the aforementioned (1) and (2) laying methods.

In addition, although not shown in the accompanying drawings, one end of the revascularization graft material is designed to be an closed end, and by using a guide wire inserted into the lumen of the revascularization graft material from the other end as an open end, the revascularization graft material may be guided to the target site in the tissue. After the revascularization graft material is inserted to the target site, the guide wire is extracted from the open end, or the closed end is cut to form an opening, and from the resulting opening, the guide wire is extracted.

The length of the guide wire is usually designed to be longer than the laying length of the revascularization graft material in the body. The length of the guide wire is appropriately set, without particularly limited, according to the type of the organ or the laying site. The material of the guide wire is not particularly limited; as the material of the guide wire, non-magnetic metals, and organic materials such as Teflon (Registered Trademark), polypropylene and polyethylene can be used.

[Laying by Sewing]

Moreover, as a method for manually laying in the tissue the revascularization graft material according to the present invention, it is also possible to adopt a method in which the revascularization graft material is sewn in the tissue as usual surgical thread. This method is suitable for laying a thin revascularization graft material.

As described above, by laying the revascularization graft material, for example, in the ischemic site, blood vessels are regenerated along the revascularization graft material. In this way, without performing the revascularization procedure involving invasiveness and risk, myocardial infarction and lower limb ischemia (mainly, diabetes) due to arterial stiffening can be possibly treated. Moreover, when vascular endothelial cells or the precursor cells thereof are implanted as attached to the revascularization graft material, or preferably as packed in the lumen of the revascularization graft material, it is also possible to regenerate long blood vessels in the target organ although with conventional methods simply injecting cells, such regeneration of long blood vessels has been almost impossible.

The implantation of the revascularization graft material of the present invention into animals can regenerate blood vessels. The animal species is not particularly limited, but is preferably human, monkey, dog, cat, rabbit, horse, sheep, mouse, rat or the like, more preferably human, monkey, dog, cat or the like, and most preferably human. The revascularization graft material can be prepared as described above, but can also be purchased.

EXAMPLES

Reference Example 1: Preparation of Hollow Tubular Structure

Around a core (polyglycolic acid fibers (PGA) of 100 and 500 μm in diameter), polyglycolic acid fibers (four to eight of single yarns of 10 μm in diameter were twisted and used) were knitted to prepare a hollow tubular structure (corresponding to an outer tube or an inner tube).

The hollow tubular structure was immersed in a 0.1N-phosphate buffer (pH7.2) containing heparin in a content of 10 μg/ml (at room temperature, for 16 hours). Next, the hollow tubular structure was washed with a phosphate buffer, and dried to prepare a heparin-binding hollow tubular structure.

The heparin-binding hollow tubular structure was immersed in a VEGF solution, and VEGF was bound to the hollow tubular structure through the intermediary of heparin.

Reference Example 2: Introduction of Gene with Gene Transfer Vector-Binding Hollow Tubular Structure The hollow tubular structure obtained in Reference Example 1 was immersed in a solution of GFP gene-incorporated adeno-associated virus (AAV) (phosphate buffer, virus concentration: $1 \times 10^2$ viral particles/ml), allowed to react at 37° C. for 1 hour, and then washed with phosphate buffer. The 293 cells were cultured all over a culture plate, the AAV-bound hollow tubular structure was placed on the cultured 293 cells, and the culture was performed for 3 weeks.

As shown in FIG. 5-1, only the cells brought into contact with the hollow tubular structure emitted green fluorescence. This shows that AAV is almost not released from the hollow tubular structure, and that AAV, in a state of maintaining the activity, was bound to the hollow tubular structure. FIG. 5-2 is a diagram schematically showing the region where the hollow tubular structure and the cells in contact with the hollow tubular structure and expressing the GFP were located in the photograph shown in FIG. 5-1.

Example 1: Implanting of Revascularization Graft Material into Muscle

Figures 1, 6:
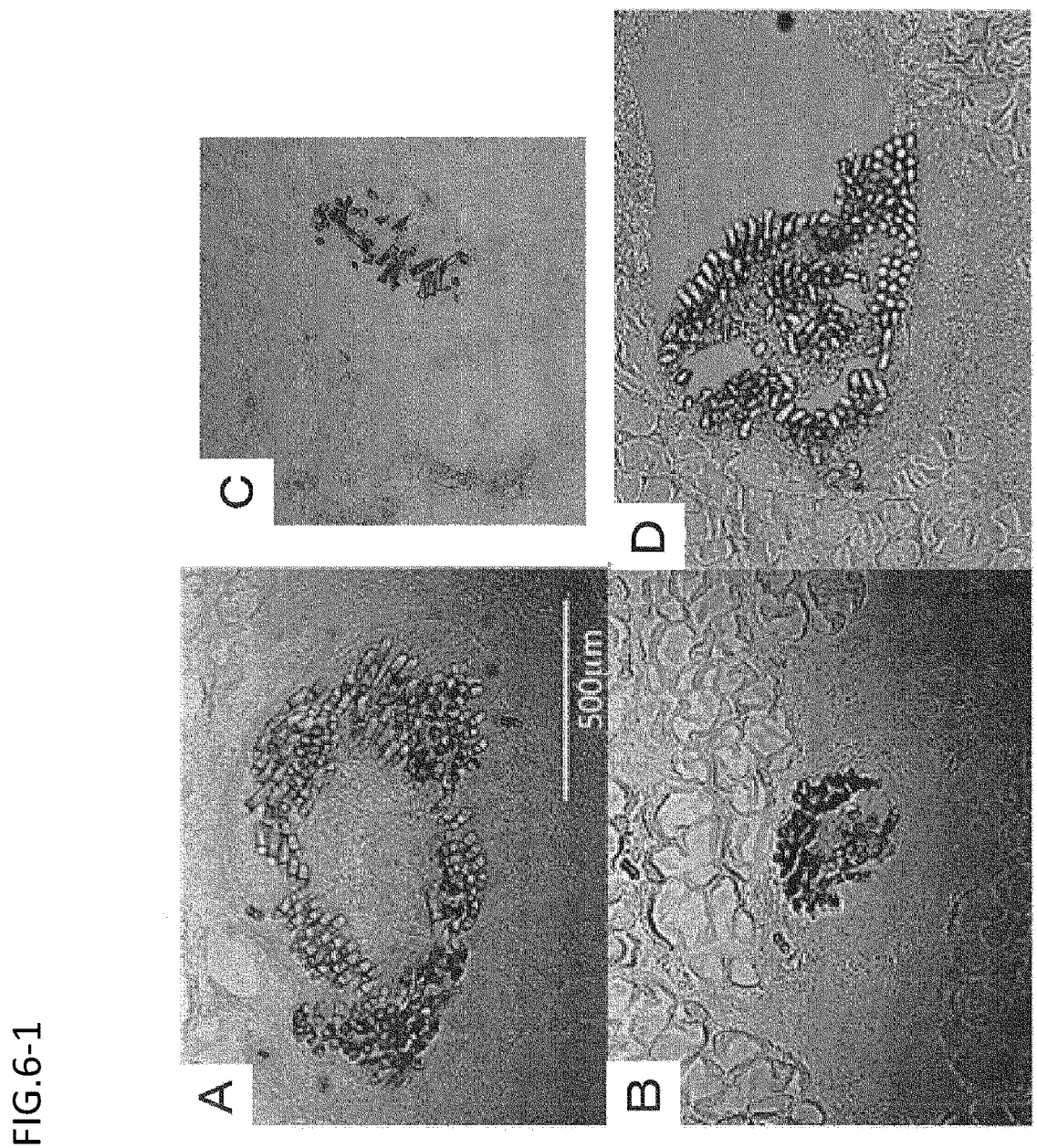

Of the hollow tubular structures having a single tubular structure, obtained in Reference Example 1 (hereinafter, in present Example and Examples 2 and 3, simply referred to as "the hollow tubular structure"), the hollow tubular structure having a lumen diameter of 500 μm and the hollow tubular structure having a lumen diameter of 100 μm were implanted by sewing these hollow tubular structures into the subcutaneous tissue of the lower limb of a rat. After 3 days, the sites with the hollow tubular structures sewn therein were sampled, and the tissue sections were prepared according to the conventional method and were observed with an optical microscope. The results thus obtained are shown in FIG. 6-1(A) and FIG. 6-1(B).

In addition, of the hollow tubular structures obtained in Reference Example 1, the hollow tubular structure having a lumen diameter of 100 μm was implanted by sewing the hollow tubular structure into a muscle of the lower limb of a rat. Moreover, of the hollow tubular structures obtained in Reference Example 1, the hollow tubular structure having a lumen diameter of 500 μm and the hollow tubular structure having a lumen diameter of 100 μm were adopted as an outer tube and an inner tube, respectively; the inner tube was inserted together with the core thereof into the lumen of the outer tube from which the core was extracted, then the core of the inner tube was extracted, and thus a hollow tubular structure (namely, a revascularization graft material) having a double-tube structure was obtained. The obtained revascularization graft material was implanted by sewing the revascularization graft material into a muscle of the lower limb of a rat. After 3 days, the sites with the hollow tubular structure and the revascularization graft material sewn therein, respectively, were sampled, and the tissue sections were prepared according to the conventional method and were observed with an optical microscope. The results thus obtained are shown in FIG. 6-1(C) and FIG. 6-1(D).

In the cases of the implantation into the subcutaneous tissue, the hollow tubular structure having a lumen diameter of 500 μm and the hollow tubular structure having a lumen diameter of 100 μm both maintained the lumens even after 3 days from the implantation (see FIG. 6-1(A) and FIG. 6-1(B), and FIG. 6-2(A) and FIG. 6-2(B) each schematically showing the hollow tubular structure and the lumen). However, in the case of the implantation into a muscle, the tubular structure having a lumen diameter of 100 μm underwent the occlusion of the lumen and the collapse of the tubular structure after 3 days from implantation (see FIG. 6-1(C) and FIG. 6-2(C)). On the other hand, it was revealed that in the revascularization graft material having a double-tube structure, the lumen space of the inner tube was able to be maintained and the space formed of the lumen internal surface of the outer tube and the external surface of the inner tube was also able to be maintained even after 3 days from the implantation into the muscle (see FIG. 6-1(D) and FIG. 6-2(D)).

Example 2: Implantation of VEGF-Coated Revascularization Graft Material into a Lower Limb Ischemia Model Mouse (Nude Mouse)

In Reference Example 1, the hollow tubular structure having a lumen diameter of 100 μm was obtained. A revascularization graft material having a double-tube structure was obtained by inserting the inner tube (lumen diameter: 100 μm) after extraction of the core into the lumen of the outer tube (lumen diameter: 500 μm) obtained in Reference Example 1, after extraction of the core.

In distilled water for injection, heparin (from Sigma) was dissolved in a content of 10 mg/ml, the hollow tubular structure and the revascularization graft material were immersed in the resulting aqueous solution of heparin (at room temperature, for 16 hours). Next, the hollow tubular structure and the revascularization graft material were washed with distilled water for injection, and thus a heparin-binding hollow tubular structure and a heparin-binding revascularization graft material were prepared.

In phosphate buffered saline, the recombinant mouse VEGF (from R&D Systems) was dissolved in a content of 5 μg/ml, the heparin-binding hollow tubular structure and the heparin-binding revascularization graft material were immersed in the resulting solution (at room temperature, for 2 hours). Next, the hollow tubular structure and the revascularization graft material were washed with phosphate buffered saline, and thus a VEGF-binding hollow tubular structure and a VEGF-binding revascularization graft material were obtained.

The implantation of the revascularization graft material into a lower limb ischemia model animal was performed as follows. A female of nude mouse (CAnN.cg-Foxn1nu, from Charles River) was subjected to general anesthesia, by intraperitoneal administration of Somnopentyl (Registered Trademark) (Kyoritsu Seiyaku). The skin of the right lower limb was incised, the femoral artery and vein were ligated immediately beneath the abdominal wall with surgical suture, and blood vessels were peeled off from the suture site to the saphenous artery and vein. Successively, the VEGF-binding hollow tubular structure or the VEGF-binding revascularization graft material was implanted by sewing the tubular structure concerned or the graft material concerned into biceps femoris muscle. The skin was sutured and the implantation site was closed.

After 3 weeks from the implantation, the female mouse was exsanguinated under avertin (2,2,2-tribromoethanol, from Sigma) anesthesia and thereby euthanized. The sites in which the scaffold material for implantation was sewn were sampled, and the obtained samples were fixed with 10% neutral buffer formalin. The paraffin sections of the tissues were prepared according to the conventional method and were subjected to staining with hematoxylin (from Muto Pure Chemicals) and eosin (from Muto Pure Chemicals). The prepared paraffin sections were observed with an optical microscope (BIOREVO X710, from Keyence).

Figure 7:
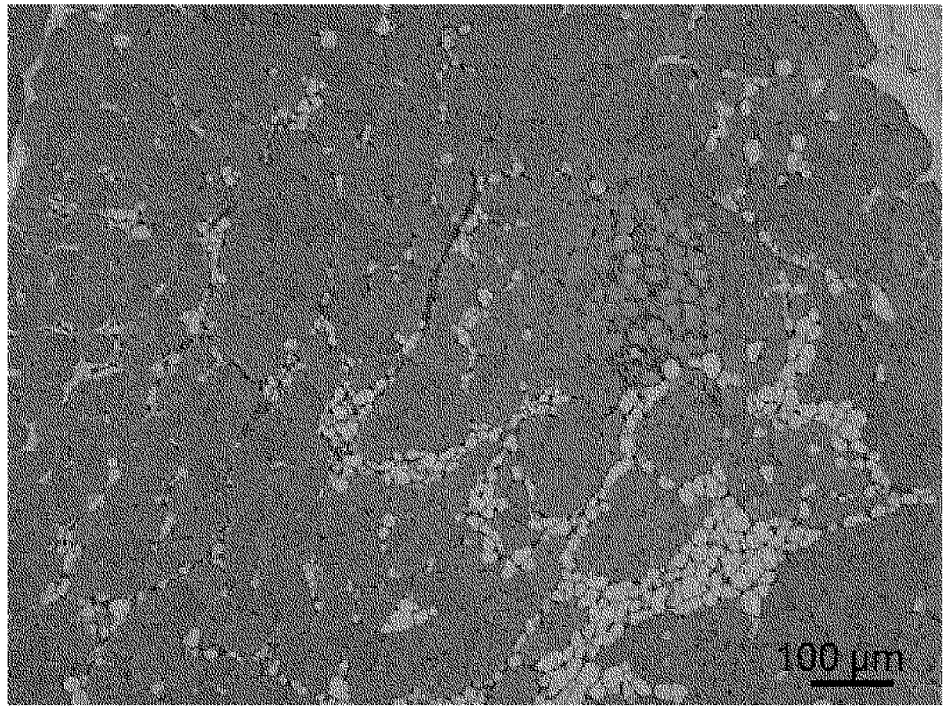
FIG. 7 is photographs showing the results (3 weeks after implantation) of the implantation of a VEGF-coated revascularization graft material into a lower limb ischemia model mouse (nude mouse), FIG. 7(A) showing the implantation region of a hollow tubular structure having a single-tube structure, and FIG. 7(B) showing the implantation region of a revascularization graft material having a double-tube structure.
Figure 7:
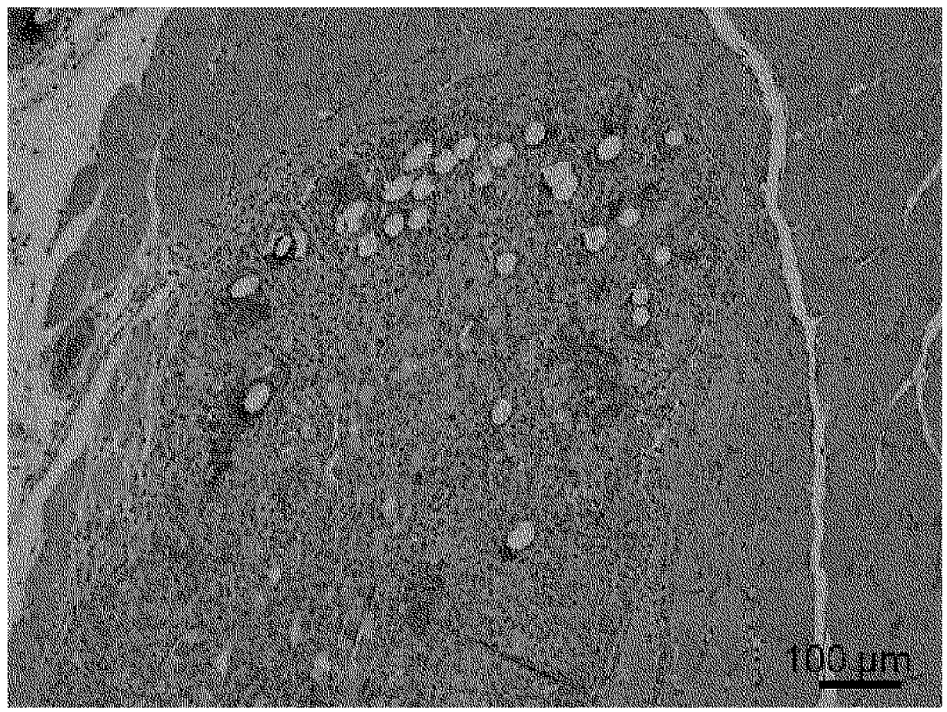

The results thus obtained are shown in FIG. 7. FIG. 7(A) shows the implantation site of the hollow tubular structure, and FIG. 7(B) shows the implantation site of the revascularization graft material. After 3 weeks from the implantation into the lower limb muscle, the hollow tubular structure having a single tubular structure underwent the occlusion of the lumen and the collapse of the tubular structure. On the other hand, it was revealed that in the case of the implantation of the revascularization graft material having a double-tube structure, the lumen space of the inner tube was able to be maintained, and the space formed of the lumen internal surface of the outer tube and the external surface of the inner tube was also able to be maintained.

Example 3: Implantation of VEGF-Coated Revascularization Graft Material into a Lower Limb Ischemia Model Mouse (C57BL/6J)

Next, experiments were performed, in another strain of mice, for the purpose of verifying the securement of the inner lumen space of the revascularization graft material, and at the same time, for the purpose of demonstrating the revascularization in the interior of the revascularization graft material. By using a female of C57BL/6J mouse (from Charles River), in the same manner as in Example 2, a lower limb ischemia model was prepared, and the VEGF-binding hollow tubular structure or the VEGF-binding revascularization graft material was implanted.

After 3 weeks from the implantation, tail vein injection of 100 μl of biotin-binding tomato lectin (from Vector Laboratories) having a content of 1 mg/ml was performed; intraperitoneal administration of avertin anesthetic was performed after 7 minutes from the injection; after 10 minutes from the injection, thoracotomy was performed, 20 ml of phosphate buffered saline was perfused, and moreover, a 2% paraformaldehyde solution was perfused.

The site in which the hollow tubular structure was sewn and the site in which the revascularization graft material was sewn were sampled, and the obtained samples were fixed with 10% neutral buffer formalin. The paraffin sections of the tissues were prepared according to the conventional method and were subjected to staining with hematoxylin and eosin. Immunohistochemistry using the anti-CD31 antibody, which is a marker for the vascular endothelial cell, was performed as follows. The activation of the antigen was performed by heat treatment in 0.5 M Tris-HCl buffer (pH10.0), blocking was performed with 10% donkey serum (from Jackson Immuno Research), and then staining was performed by using rabbit anti-CD31 antibody (from Abcam), enbision kit+/HRP anti-rabbit (from Dako) and DAB+(3,3'-diaminobenzidine tetrahydrochloride) substrate kit. In order to detect the biotin-binding tomato lectin injected by vein injection, activation of the antigen was performed by heat treatment in a 1-mM EDTA solution, blocking was performed with 5% skim milk (from BD Biosciences), and then staining was performed by using horseradish peroxidase (HRP) labeled streptavidin (from Thermo Scientific) and DAB+substrate kit (from Dako). The prepared paraffin sections were observed with an optical microscope (BIOREVO X710, from Keyence).

Figure 8:
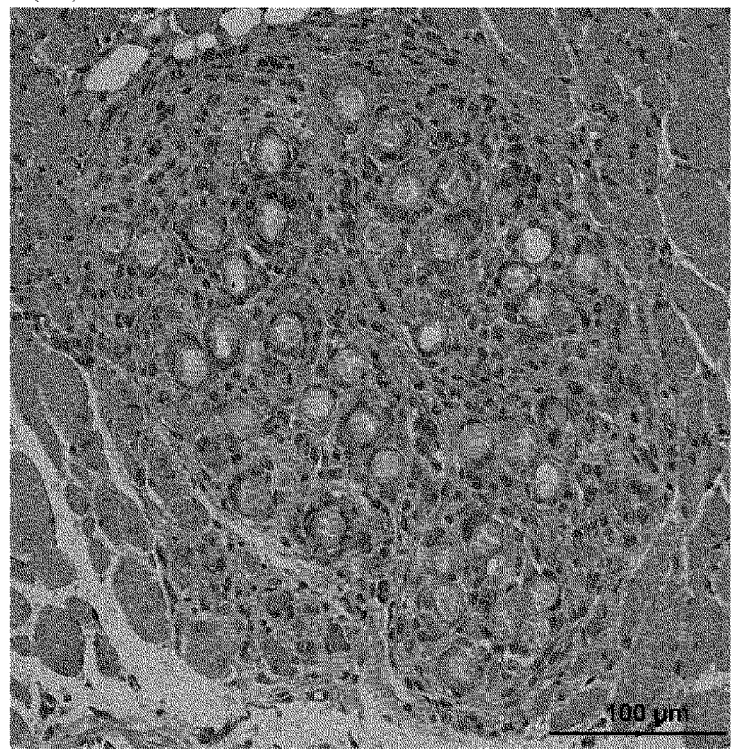
FIG. 8 is photographs showing the results (3 weeks after implantation) of the implantation of a VEGF-coated revascularization graft material into a lower limb ischemia model mouse (C57BL/6J), FIG. 8(A) showing the implantation region of a hollow tubular structure having a single-tube structure, and FIG. 8(B) showing the implantation region of a revascularization graft material having a double-tube structure.
Figure 8:
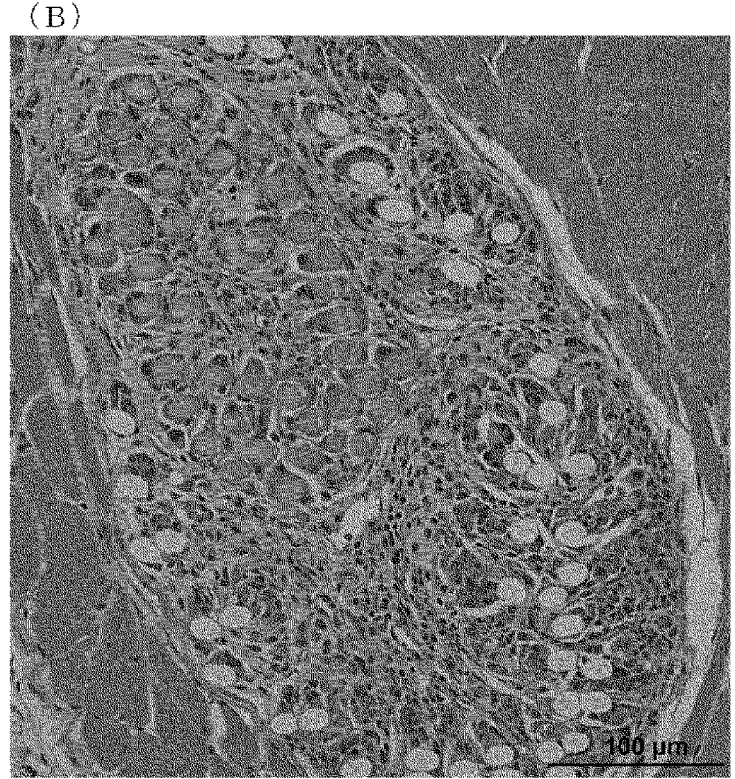

The results thus obtained are shown in FIG. 8. FIG. 8(A) shows the implantation site of the hollow tubular structure, and FIG. 8(B) shows the implantation site of the revascularization graft material. After 3 weeks from the implantation in the lower limb muscle, the hollow tubular structure having a single tubular structure underwent a partial occlusion of the lumen. On the other hand, it was revealed that in the case of the implantation of the revascularization graft material having a double-tube structure, the lumen space of the inner tube was able to be maintained, and the space formed of the lumen internal surface of the outer tube and the external surface of the inner tube was also able to be maintained. The usefulness of the revascularization graft material having a double-tube structure was revealed from the results after 3 days from the implantation in Example 1, and additionally, from the results after 3 weeks from the implantation in Examples 2 and 3.

Figure 9:
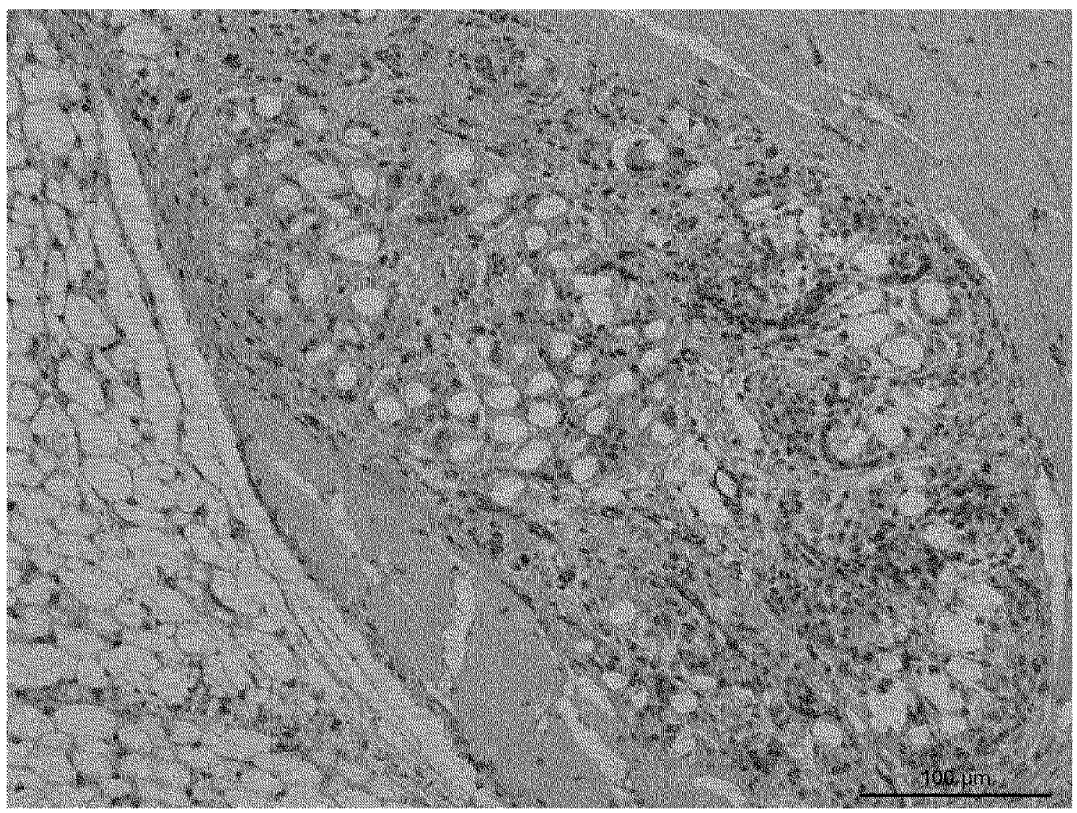
FIG. 9 is a photograph showing the CD31 chromatic figure of the implantation region of the revascularization graft material in a lower limb ischemia model mouse (C57BL/6J).

By performing the staining of CD31, the revascularization in the interior of the revascularization graft material having a double-tube structure was verified. The results thus obtained are shown in FIG. 9. It was revealed that the CD31 positive blood vessels were formed in the lumen space of the inner tube, and also in the space formed of the lumen internal surface of the outer tube and the external surface of the inner tube.

Figure 10:
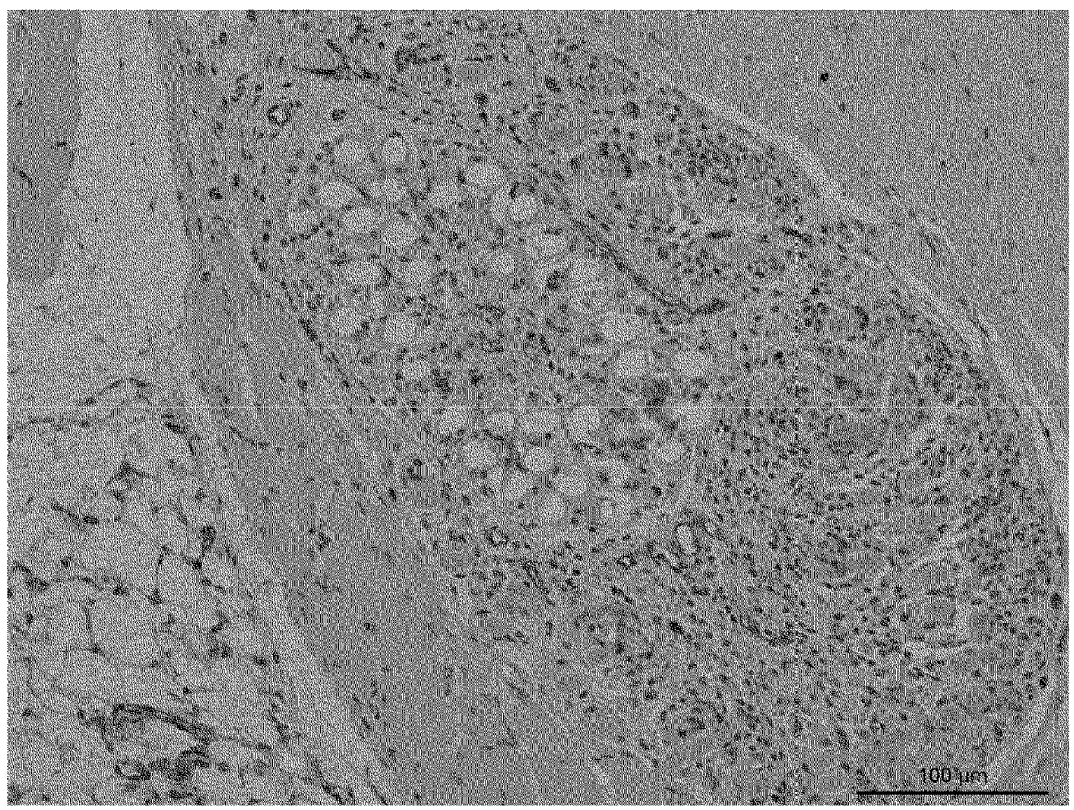
FIG. 10 is a photograph showing the binding of tomato lectin in the implantation region of the revascularization graft material in a lower limb ischemia model mouse (C57BL/6J).

By detecting the biotin-binding tomato lectin injected by vein injection, the functional revascularization involving blood flow in the interior of the revascularization graft material having a double-tube structure was evaluated. The results thus obtained are shown in FIG. 10. It was revealed that functional blood vessels to be positive to the tomato lectin injected by vein injection were formed in the lumen space of the inner tube, and also in the space formed of the lumen internal surface of the outer tube and the external surface of the inner tube.

INDUSTRIAL APPLICABILITY

The revascularization graft material according to the present invention is useful for the regenerative medicine of blood vessels aiming at the treatment of the vascular disorder due to complication of diabetes, cancer, rheumatism and the like.

REFERENCE SIGNS LIST

1: outer tube, 2, 2a, 2b, 2c: inner tube, 2d: first inner tube, 2e: second inner tube, 3: biodegradable single yarn, 4: twisted yarn, 5: void, 11, 22d: space

The invention claimed is:

1. A revascularization graft material comprising an outer tube and one or more inner tubes, wherein there is provided, in the lumen of the outer tube, the one or more inner tubes, each of the one or more inner tubes having an outer diameter smaller than the lumen diameter of the outer tube, wherein each of the outer and inner tubes has a hollow tubular structure consisting of a knit of twisted yarns of biodegradable single yarns, wherein in the lumen of the outer tube an empty space is present between the lumen internal surface of the outer tube and the external surfaces of the inner tubes, and wherein the outer tube is configured to interact with tissue upon implantation at an implantation site in a living body.

2. The graft material according to claim 1, wherein to the outer tube and the inner tubes, one or more factors selected from the group consisting of vascular endothelial growth factor (VEGF), platelet-derived growth factor (PDGF), fibroblast growth factor (FGF) and/or hepatocyte growth factor (HGF) are bound.

3. The graft material according to claim 1, wherein one or more factors selected from the group consisting of vascular endothelial growth factor (VEGF), platelet-derived growth factor (PDGF), fibroblast growth factor (FGF) and hepatocyte growth factor (HGF) are bound to the outer tube, and one or more different factors selected from the group are bound to the inner tubes.

4. The graft material according to claim 3, wherein one or more factors selected from the group consisting of platelet-derived growth factor (PDGF), fibroblast growth factor (FGF) and hepatocyte growth factor (HGF) are bound to the outer tube, and vascular endothelial growth factor (VEGF) is bound to the inner tubes.

5. The graft material according to claim 3, wherein vascular endothelial growth factor (VEGF) is bound to the outer tube, and one or more factors selected from the group consisting of platelet-derived growth factor (PDGF), fibroblast growth factor (FGF) and hepatocyte growth factor (HGF) are bound to the inner tubes.

6. The graft material according to claim 1, wherein vascular cells and/or cells to differentiate into vascular cells are packed in the lumen of the inner tubes and/or the space.

7. The graft material according to claim 1, wherein the outer tube and the inner tubes have voids being formed between the twisted yarns of the knit, and the voids allows the exterior and the interior of the lumen to communicate with each other.

8. The graft material according to claim 1, wherein a plurality of inner tubes are provided in the lumen of the outer tube.

9. The graft material according to claim 8, wherein to the outer tube and the inner tubes, one or more factors selected from the group consisting of vascular endothelial growth factor (VEGF), platelet-derived growth factor (PDGF), fibroblast growth factor (FGF) and/or hepatocyte growth factor (HGF) are bound.

10. The graft material according to claim 8, wherein one or more factors selected from the group consisting of vascular endothelial growth factor (VEGF), platelet-derived growth factor (PDGF), fibroblast growth factor (FGF) and hepatocyte growth factor (HGF) are bound to the outer tube, and one or more different factors selected from the group are bound to the inner tubes.

11. The graft material according to claim 10, wherein one or more factors selected from the group consisting of platelet-derived growth factor (PDGF), fibroblast growth factor (FGF) and hepatocyte growth factor (HGF) are bound to the outer tube, and vascular endothelial growth factor (VEGF) is bound to the inner tubes.

12. The graft material according to claim 10, wherein vascular endothelial growth factor (VEGF) is bound to the outer tube, and one or more factors selected from the group consisting of platelet-derived growth factor (PDGF), fibroblast growth factor (FGF) and hepatocyte growth factor (HGF) are bound to the inner tubes.

13. The graft material according to claim 8, wherein vascular cells and/or cells to differentiate into vascular cells are packed in the lumen of the inner tubes and/or the space.

14. The graft material according to claim 8, wherein the outer tube and the inner tubes have voids being formed between the twisted yarns of the knit, and the voids allows the exterior and the interior of the lumen to communicate with each other.

15. The graft material according to claim 1, wherein the number of the inner tubes is two, and a second inner tube is further provided in the lumen of a first inner tube provided in the lumen of the outer tube.

16. The graft material according to claim 15, wherein to the outer tube and the inner tubes, one or more factors selected from the group consisting of vascular endothelial growth factor (VEGF), platelet-derived growth factor (PDGF), fibroblast growth factor (FGF) and/or hepatocyte growth factor (HGF) are bound.

17. The graft material according to claim 15, wherein one or more factors selected from the group consisting of vascular endothelial growth factor (VEGF), platelet-derived growth factor (PDGF), fibroblast growth factor (FGF) and hepatocyte growth factor (HGF) are bound to the outer tube, and one or more different factors selected from the group are bound to the inner tubes.

18. The graft material according to claim 15, wherein vascular cells and/or cells to differentiate into vascular cells are packed in the lumen of the inner tubes and/or the space.

19. The graft material according to claim 15, wherein the outer tube and the inner tubes have voids being formed between the twisted yarns of the knit, and the voids allows the exterior and the interior of the lumen to communicate with each other.

20. The graft material according to claim 1, wherein the number of the inner tubes is one.

21. The graft material according to claim 20, wherein to the outer tube and the inner tube, one or more factors selected from the group consisting of vascular endothelial growth factor (VEGF), platelet-derived growth factor (PDGF), fibroblast growth factor (FGF) and/or hepatocyte growth factor (HGF) are bound.

22. The graft material according to claim 20, wherein one or more factors selected from the group consisting of vascular endothelial growth factor (VEGF), platelet-derived growth factor (PDGF), fibroblast growth factor (FGF) and hepatocyte growth factor (HGF) are bound to the outer tube, and one or more different factors selected from the group are bound to the inner tube.

23. The graft material according to claim 20, wherein vascular cells and/or cells to differentiate into vascular cells are packed in the lumen of the inner tube and/or the space.

24. The graft material according to claim 20, wherein the outer tube and the inner tube have voids being formed between the twisted yarns of the knit, and the voids allows the exterior and the interior of the lumen to communicate with each other.

* * * * *